(12) United States Patent
Thoma et al.

(10) Patent No.: US 6,677,164 B1
(45) Date of Patent: Jan. 13, 2004

(54) MULTIVALENT POLYMERS, PROCESSES FOR THEIR PREPARATION, AND THEIR USE FOR PREPARING BIOLOGICALLY ACTIVE COMPOUNDS

(75) Inventors: Gebhard Thoma, Lörrach (DE); Rudolf Duthaler, Bettingen (CH); Beat Ernst, Magden (CH); John Louis Magnani, Rockville, MD (US); John Tinsman Patton, Jr., Gaithersburg, MD (US)

(73) Assignee: Novartis AG, Basel (CH)

(*) Notice: Subject to any disclaimer, the term of this patent is extended or adjusted under 35 U.S.C. 154(b) by 0 days.

(21) Appl. No.: 09/068,882

(22) PCT Filed: Nov. 12, 1996

(86) PCT No.: PCT/EP96/04938
§ 371 (c)(1),
(2), (4) Date: Jun. 11, 1998

(87) PCT Pub. No.: WO97/19105
PCT Pub. Date: May 29, 1997

(30) Foreign Application Priority Data

Nov. 21, 1995 (CH) .................................. 3297/95

(51) Int. Cl.$^7$ ............... G01N 33/533; G01N 33/546; G01N 33/535; C07K 17/06; A61K 39/44
(52) U.S. Cl. .............. 436/546; 424/93.7; 424/179.1; 435/6; 435/7.2; 435/7.21; 435/7.5; 435/7.95; 436/501; 436/533; 436/534; 436/827; 436/909; 530/391.1; 530/391.9; 530/402; 530/404
(58) Field of Search ............................ 436/546, 534, 436/533, 501, 909, 827; 435/7.21, 7.2, 7.5, 7.95, 6; 530/402, 404, 391.1, 391.9; 424/179.1, 93.7

(56) References Cited

U.S. PATENT DOCUMENTS 5,066,716 A   11/1991   Robey et al. ................. 525/54

FOREIGN PATENT DOCUMENTS

| DE | 3612102 | 10/1986 |
| EP | 0601417 | 6/1994 |
| WO | 90/02558 | 3/1990 |
| WO | 92/07572 | 5/1992 |
| WO | 92/19735 | 11/1992 |
| WO | 92/22318 | 12/1992 |
| WO | 94/11005 | 5/1994 |

OTHER PUBLICATIONS

Arar et al., "Synthesis and Antiviral Activity of Peptide–Oligonucleotide Conjugates Prepared by Using Nα–(Bromoacetyl)peptides", Bioconjugate Chem., vol. 6, 1995 pp. 573–577.

Catterall, William A., Functional Subunit Structure of Voltage–Gated Calcium Channels, Sep. 27, 1991.

Cruse and Lewis (Eds. Conjugate Vaccines) Contrib. Microbiol. Immunol., vol. 10, 1989, pp. 1–10.

Dasgupta et al., "Anti–adhesive Therapeutics: a New Class of Anti–inflammatory Agents", Exp. Opin. Invest. Drugs, vol. 3, 1994, pp. 709–724.

Giammona et al., "Anticancer Agent Coupled to Polyaspartamide as a Drug Carrier", Eur. J. Pharm. Biopharm, vol. 38, 1992, pp. 159–162.

Giammona et al., "Polymeric prodrugs: α,β–poly (N–hydroxyethyl)–DL–aspartamide as a Macromolecular Carrier for Some Non–steroidal Anti–inflammatory Agents", Int. J. Pharmaceutics, vol. 57, 1989, pp. 55–62.

Inman, John K., "Syntheses of Macromolecular Immunomodulators and Conjugates Employing Haloacetyl Reagents", Annals New York Acad. Sci., vol. 685, 1993, pp. 347–350.

Janata, Jiri, "Principles of Chemical Sensors", Plenum Press, New York, 1989, pp. 14–29.

Kennedy, J.F., and White, C.A., Classification and Description of Monosaccharides, oligosaccharides, and polysaccharides, Clarendon Press, Oxford, 1988, pp. 3–41.

Kopecek, J., and Duncan, R., "Targetable Polymeric Prodrugs", J. Controlled Release, vol. 6, 1987, pp. 315–327.

Lees et al., "Polyacrylamides Bearing Pendant α–Sialoside Groups Strongly Inhibit Agglutination of Erythrocytes by Influenza A Virus: Multivalency and Steric Stabilization of Particulate Biological Systems", J. Med. Chem. vol. 37, 1994, pp. 3419–3433.

Lu et al., "Chemically Unambiguous Peptide Immunogen: Preparation, Orientation and Antigenicity of Purified Peptide Conjugated to the Multiple Antigen Peptide System", Mol. Immunol. vol. 28, 1991, pp. 623–630.

Nifant'ev et al., "Synthetic Probe for Study of Molecules Related to Selectin Family", Synthetic Oligosaccharides, ACS Symposium Series 560, 1994, pp. 267–275.

Paulson, James C., "Interactions of Animal Viruses with Cell Surface Receptors", The Receptors II, Conn (Ed.), Academic Press, 1985, p. 131–219.

Roy et al., "Solid–phase Synthesis of Dendritic Sialoside Inhibitors of Influenza A Virus Haemagglutinin", J. Chem. Soc., Chem. Comm., 1993, pp. 1869–1872.

Schneerson et al., "Vaccines Composed of Polysaccharide–protein Conjugates: Current Status, Unanswered Questions, and Prospects for the Future", Towards Better Carbohydrate Vaccines, Bell and Torrigiani (Eds.), John Wiley & Sons, Chichester, 1987, pp. 307–327.

(List continued on next page.)

Primary Examiner—Mary E. Ceperley
(74) Attorney, Agent, or Firm—David E. Wildman

(57) ABSTRACT

The present invention provides biologically active linear polypeptides that possess a plurality of biologically active groups, methods employing such peptides to target molecules to cells, and methods employing such peptides for inhibiting the binding of cells to each other.

13 Claims, No Drawings

OTHER PUBLICATIONS

Spaltenstein, A., and Whitesides, G. M., "Polyacrylamides Bearing Pendant α–Sialoside Groups Strongly Inhibit Agglutination of Erythrocytes by Influenza Virus", vol. 113, 1991, pp. 686.

Strömberg et al., "Host–specificity of uropathogenic *Escherichia coli* depends on differences in binding specificity to Galα1–4 Gal–containing isoreceptors", EMBO J., vol. 9, 1990, pp. 2001–2010.

Uhlmann E., and Peyman, A., "Antisense Oligonucleotides: A new therapeutic Principle", Chemical Reviews, vol. 90, 1990, pp. 543–584.

Zaitsu et al., "New Heterobifunctional Cross–Linking Reagents for Protein Conjugation, N–(Bromoacetamido–n–alkanoyloxy)succinimides", Chem. Pharm. Bull., vol. 35, 1991, pp. 1991–1997.

Zorc, B. and Butula, I., "Macromolecular prodrugs. III. Esters of fenoprofen and probenecid", Acta Pharm., vol. 44, 1994, pp. 103–108.

Zorc et al., "Macromolecular prodrugs. II. Esters of L–dopa and α–methyldopa", Int. J. Pharmaceutics, vol. 99, 1993, pp. 135–143.

MULTIVALENT POLYMERS, PROCESSES FOR THEIR PREPARATION, AND THEIR USE FOR PREPARING BIOLOGICALLY ACTIVE COMPOUNDS

This application is a 371 of PCT/EP96/04938, filed Nov. 21, 1995, abandoned.

The present invention relates to biologically degradable polypeptides which possess active halogen atoms which are covalently bound to side chains; to such polypeptides which possess recognition molecules and/or water-soluble groups which are bound in the side chains; and also to processes for their preparation by reacting polyamides which contain functional groups with halomethylcarbonylating agents or reacting the polypeptides which contain active halogen atoms with this group-containing recognition molecules or water-soluble groups; and to the use of these polymers in therapeutic compositions or in the active layer of diagnostic agents.

Receptor-ligand interactions are of great importance in intracellular communication and in intercellular recognition processes. The initiation of diseases, for example bacterial diseases [J. C. Paulson, The receptors, Vol. II, Ed.: P. M. Conn, Academic Press, 1985, 131], viral Infections [Strömberg et al. EMBO J. 1990, (9), 2001] and inflammatory diseases [Dasgupta, F., Rao, B. N. N., Exp. Opin. Invest. Drugs 3:709–724 (1994)] takes place by way of ligand-receptor interactions. In specified examples, the ligands are oligosaccharides. It is not possible to use free oligosaccharides, which are to bind to receptors in place of natural ligands, for the therapy of these diseases because of the very high quantities of oligosaccharides which have to be administered since the affinity between the receptors and the ligands is too low.

It is known that an increased interaction between receptor and ligand is achieved by coupling several ligands on a surface. The example of the viral protein haemagglutinine, binding to neuramic acid on the cell surface and their interaction has been used to show how this polyvalent effect obtained by using a polymer affects such an interaction [A. Spaltenstein et al. *J. Am. Chem. Soc.* 1991 (113) 686].

Polymeric compounds which present ligands in multivalent form can lead, in ligand-receptor recognition processes, to increased interactions with receptors and be used therapeutically, for example as receptor blockers [W. J. Lees et.al., *J. Med. Chem.* 1994, 37, 3419; EP 601417 A2] or multivalent enzyme inhibitors [WO 90/02558].

Other applications have also been reported for polymers which are functionalized by defined quantities of active molecules. For targeting active substances, use can be made of more complex polymers which, in addition to active compounds, also carry substances which are selectively recognized by particular cell-surface receptors so that these active compounds are preferentially transported to these types of cells [J. Kopecjek, R. Duncan, J. Controlled Release 1987, 6, 315].

In addition, active compounds which are coupled covalently to polymers by way of labile bonds can be selectively released in the organism at sights where these bonds are cleaved by particular physiological conditions [B. Zorc et. al., Acta Pharm. 1994, 44,103; B.Zorc et. al., Int. J. Pharmaceutics 1993, 99, 135; G. Giammona et. al., Eur. J. Pharm. Biopharm. 1992, 38, 159; G. Giammona et. al., Eur. J. Pharm Biopharm. 1992, 38, 159; G. Giammona et. al. Int J. Pharmaceutics 1989, 57, 55].

Polymers which are functionalized by receptor molecules or ligands can be widely used in diagnostics. Immobilized marker molecules, for example biotin, can be used when carrying out biological tests [N. E. Nifant'ev et. al., in "Synthetic Oligosaccharides", Ed.: P. Kovac, ACS Symposium Series 560, Washington, D.C. 1994)]. Compounds of this nature can be present as recognition elements in the active layers of sensors [Janata, Principles of Chemical Sensors, Plenum Press, New York 1989].

Immobilized active molecules can also be antigens which can be employed as vaccines [Conjugate Vaccines, Eds.: J. M. Cruse, R. E. Lewis, Jr; Karger, Basel 1989; Towards Better Carbohydrate Vaccines, Eds.: R. Bell, G. Torrigiani, John Wiley & Sons, Chichester 1987].

EP 0601417 A2 already discloses a mixture in which physiologically tolerated and physiologically degradable polymer-based carbohydrate receptor blockers are prepared. These blockers consist of a carbohydrate moiety, a bifunctional spacer, a hydrophilic polymer and an effect enhancer. However, it is not possible to incorporate all or some of the carbohydrate ligands in a specific manner or even to incorporate different ligands in a specific manner.

For the purpose of constructing complex polymers in a controlled manner, small quantities of an active substance can be coupled to a preformed polymer which carries an excess of activated side chains. This principle was exploited for synthesizing polymeric, water-soluble neoglycoconjugates which are based on nitrogen-substituted polyacrylamides [WO 94/11005-A1; N. V. Bovin et. al., *Glycoconjugate J.* 1993, 10, 142; N. E. Nifant'ev et al., in "Synthetic Oligosaccharides", Ed.: P. Kovac, ACS Symposium Series 560, Washington, D.C. 1994]. However, the scope for using such compounds is limited by the fact that the polymer backbone is not necessarily biodegradable.

It has now been found, surprisingly, that biodegradable polymers which possess side chains which are functionalized identically or differently can be specifically obtained with a precisely defined, predictable composition when polypeptides which possess activated halogen atoms in the side chains are used as the starting material and are reacted with substituents which contain a mercapto group. In addition, these polypeptides can be prepared in a simple manner and in high yields and purities. Water-soluble, gelatinous or water-insoluble potypeptides can be obtained depending on the hydrophilicity of the substituents. It is particularly worth mentioning that precisely defined active compound densities can be set and it is possible, concomitently to carry out further modification which is controlled in accordance with the desired application. The polypeptides which contain activated halogen atoms are also surprisingly easy to obtain, very stable and readily soluble in various organic solvents.

The invention relates to polypeptides which possess identical or different structural elements of the formula (I),

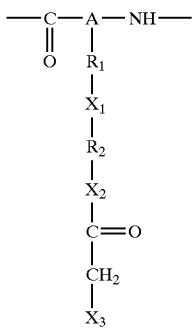
(I), in which
A is a trivalent, aliphatic hydrocarbon radical having from 1 to 12 C atoms which is unsubstituted or substituted by one or more substituents selected from the group consisting of $C_1$–$C_4$alkyl, $C_1$–$C_4$alkoxy, $C_1$–$C_4$alkylthio, benzyl and benzyloxy, $R_1$ is a direct bond or $C_1$–$C_6$alkylene, $X_1$ is —C(O)O—,—C(O)NR—, —NR—, —S— or —O—;

$R_2$ is a bivalent bridging group, $X_2$ is O or NR, or $R_2$ and $X_2$ are together a direct bond, $X_3$ is a halogen, and R is H or $C_1$–$C_6$alkyl;

with the proviso that $X_1$ is not —NR—, —S— or —O— when $R_1$ is a direct bond.

As halogen, $X_3$ is preferably Cl, Br or I, and particularly preferably Cl or Br.

The trivalent radical A preferably contains from 1 to 8, more preferably from 1 to 6, particularly preferably from 1 to 4 and, in particular, 1 or 2, C atoms. Examples are 1,1,6-, 1,2,6-, 1,3,6-, 1,4,6-, 1,5,6- or 1,6,6-hexanetriyl, 1,1,5-, 1,2,5-, 1,3,5-, 1,4,5- or 1,5,5-pentanetriyl, 1,1,4-, 1,2,4-, 1,3,4- or 1,4,4-butanetriyl, 1,1,3-, 1,2,3- or 1,3,3-propanetriyl, 1,1,2- or 1,2,2-ethanetriyl and methanetriyl. Methanetriyl and 1,1,2- and 1,2,2-ethanetriyl are particularly preferred.

As alkylene, $R_1$ preferably contains from 1 to 6 C atoms, more preferably 1–4 C atoms, which can be linear or branched. Examples are 1,6-, 1,5-, 1,4-, 1,3-, 1,2-, 2,3-, 2,4-, 2,5-, 2,6-, 3,4-, 3,5- or 3,6-hexylene, 1,5-, 1,4-, 1,3-, 1,2-, 2,3-, 2,4-, 2,5-, 3,4- or 3,5-pentylene, 1,4-, 1,3-, 1,2-, 2,3-, 2,4- or 3,4-butylene, 1,3-, 1,2- or 2,3- propylene, 1,2-ethylene and methylene. $R_1$ is particularly preferably linear and is especially preferably methylene, ethylene, 1,3 propylene or 1,4-butylene.

Within the scope of the present invention, $X_1$ is preferably NR or —C(O)—NR—, with R particularly preferably being H.

The bridging group can contain from 1 to 30, more preferably from 1 to 20, particularly preferably from 1 to 12, and especially preferably from 1 to 8, atoms selected from the group C, O, S, P and N. The bivalent bridging group $R_2$ can be $C_2$–$C_8$hydrocarbon radicals which are interrupted by an —NH—C(O)— group or be $C_2$–$C_8$hydrocarbon radicals which are covalently bound by way of an —NH— group. The bridging group is preferably hydrocarbon radicals which can be interrupted by one or more heteroatoms from the group O, S, P and N, and/or by —C(O)—O—, C(O)—N—, —O—C(O)—O—, —N—C(O)—N— and —C(O)—O— groups.

The bridging group can, for example, conform to the formula (VI),

—$R_4$—$X_5$—($R_5$)$_r$—($X_4$)$_s$—$R_6$— (VI), in which $X_5$ and $X_4$ are, independently of each other, a direct bond, or $X_5$ and $X_4$ are, independently of each other, —O—, —S—, —NR$_7$—,—C(O)—O—, —O—C(O)—, —O—C(O)—O—, —SO$_2$—O—, —O—SO$_2$—, —O—SO$_2$—O, —NR$_7$—C(O)—, —C(O)—NR$_7$—, —NR$_7$—C(O)—O—, —O—C(O)—NR$_7$—, —NR$_7$—C(O)—NR$_7$—, —NR$_7$SO$_2$—, —SO$_2$—NR$_7$—, —NR$_7$—SO$_2$—O—, —O—SO$_2$NR$_7$—, —NR$_7$SO$_2$—NR$_7$— or

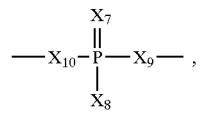

$R_5$ is a bivalent bridging group, $R_7$ is H, $C_1$–$C_{12}$alkyl, $C_5$- or $C_6$cycloalkyl, $C_5$- or $C_6$cycloalkylmethyl or -ethyl, phenyl, benzyl or 1-phenyleth-2-yl, $R_4$ and $R_6$ are, independently of each other, a direct bond, $C_1$–$C_{18}$alkylene, $C_5$- or $C_6$-cycloalkylene, $C_6$–$C_{10}$arylene or $C_7$–$C_{12}$aralkylene, r is the numbers 0 or 1 and s is the numbers 0 or 1, and s is 0 when r is 0, $X_8$ is OH, its salts, for example alkali metal, alkaline earth metal or ammonium salts (Na, K, Ca, Mg), or NR$_8$R$_9$, and $X_9$ and $X_{10}$ are, independently of each other, O or NR$_8$, with R$_8$ and R$_9$ being, independently of each other, H, $C_1$–$C_{12}$alkyl, $C_5$- or $C_6$cycloalkyl, $C_5$- or $C_6$-cycloalkylmethyl or -ethyl, phenyl, benzyl or 1-phenyleth-2-yl.

In the meaning of alkyl, $R_7$ preferably contains from 1 to 6, and particularly preferably from 1 to 4, C atoms. Some examples are methyl, ethyl, n- or i-propyl, butyl, hexyl and octyl. In the meaning of cycloalkyl, $R_7$ is preferably cyclohexyl, and cyclohexylmethyl in the meaning of cycloalkylmethyl. In a preferred embodiment, $R_7$ is H or $C_1$–$C_4$alkyl.

The bivalent bridging group is preferably a hydrocarbon radical which preferably contains from 1 to 30, more preferably from 1 to 18, particularly preferably from 1 to 12 and especially preferably from 1 to 8, C atoms and which is unsubstituted or substituted once or more than once by $C_1$–$C_4$alkyl, $C_1$–$C_4$alkoxy or =O. The hydrocarbon radical can also be interrupted once or more than once by heteroatoms selected from the group —O—, —S— and —NR$_2$—, with $R_2$ preferably being H or $C_1$–$C_4$alkyl.

The bivalent bridging group can, for example, be $C_1$–$C_{20}$—, preferably $C_2$–$C_{12}$—, alkylene which can be linear or branched. Some examples are methylene, ethylene, 1,2- or 1,3-propylene, 1,2-, 1,3- or 1,4-butylene, pentylene, hexylene, octylene, dodecylene, tetradecylene, hexadecylene and octadecyiene.

The bivalent bridging group can, for example, be polyoxaalkylene having from 2 to 12, preferably from 2 to 6, and particularly preferably from 2 to 4, oxaalkylene units and from 2 to 4, preferably 2 or 3, C atoms in the alkylene. Particularly preferably, the bridging group is polyoxaethylene and polyoxapropylene having, for example, from 2 to 6 oxaalkylene units in the bridging group.

The bivalent bridging group can, for example, be $C_5$–$C_{12}$—, preferably $C_5$–$C_8$—, and particularly preferably $C_5$- or $C_6$cycloalkylene, for example cyclopentylene, cyclohexylene, cyclooctylene or cyclododecylene.

The bivalent bridging group can, for example, be $C_5$–$C_{12}$—, preferably $C_5$–$C_8$—, and particularly preferably $C_5$- or $C_6$cycloalkyl-$C_1$–$C_{12}$— and preferably —$C_1$–$C_4$-alkylene. Some examples are cyclopentylene-$C_nH_{2n}$— and cyclohexylene-$C_nH_{2n}$—, in which n is a number from 1 to 4. Cyclohexylene-$CH_2$— is particularly preferred.

The bivalent bridging group can, for example, be $C_6$–$C_{14}$arylene and preferably $C_6$–$C_{10}$arylene, for example naphthylene or, more preferably, phenylene.

The bivalent bridging group can, for example, be $C_7$–$C_{20}$aralkylene and preferably $C_7$–$C_{12}$aralkylene. Greater preference is given to arylene-$C_nH_{2n}$—, in which arylene is naphthylene and, particularly, phenylene, and n is a number from 1 to 4. Examples are benzylene and phenylethylene.

The bivalent bridging group can, for example, be arylene-($C_nH_{2n}$—)$_2$—, in which arylene is preferably naphthylene and especially phenylene, and n is a number from 1 to 4. Examples are xylylene and phenylene($CH_2CH_2$)$_2$—.

The hydrophilicity of the polymers can be adjusted by the choice of the bivalent bridging groups. In a preferred embodiment, the bridging group is an oxaalkylene or a polyoxaalkylene preferably having from 2 to 4 C atoms, particularly preferably 2 or 3 C atoms, in the alkylene and from 2 to 20, preferably from 2 to 10, alkylene units. Particular preference is given to oxaethylene and polyoxaethylene having from 2 to 20, preferably from 2 to 10, oxaethylene units.

Within the scope of the present invention, $X_2$ is preferably O.

In a preferred embodiment, $R_2$—$X_2$ is a direct bond.

In its meaning as alkyl, R preferably contains 1–4 C atoms. Examples are methyl, ethyl and the isomers of propyl and butyl. R is preferably H.

A preferred subgroup of the novel polypeptides contains structural elements of the formula Ia,

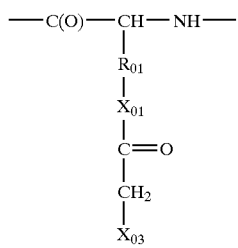

(Ia), in which $R_{01}$ is linear $C_2$–$C_6$—, and particularly preferably $C_2$–$C_4$alkylene, $X_{01}$ is the group —NH—, and $X_{03}$ is Cl or Br.

The novel polypeptides can be homopolymers, copolymers having at least two structural elements of the formula I, or copolymers additionally having comonomer units of other aminocarboxylic acids. The copolymers can be block polymers or statistical polymers.

In one embodiment of the subject-matter of the invention, the polypeptides having the structural elements of the formula (I) additionally contain at least one structural element of the formula (II), or additionally contain at least two different structural elements of the formula II,

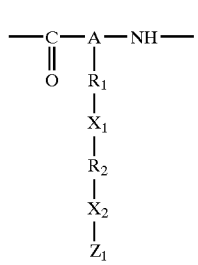

(II), in which $Z_1$ is H or $M_y$,

A, $R_1$, $X_1$, $R_2$ and $X_2$ are as defined above and y is 1 and M is a monovalent metal or y is ½ and M is a divalent metal; including their physiologically tolerated salts.

In another embodiment of the subject-matter of the invention, the polypeptides having the structural elements of the formula (I) and, if desired, structural elements of the formula II additionally contain at least one structural element of the formula (IV), or at least two different structural elements of the formula IV,

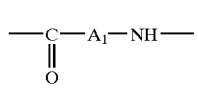

(IV), in which $A_1$ is a divalent aliphatic hydrocarbon radical having from 1 to 12 C atoms which is unsubstituted or substituted by one or more substituents selected from the group consisting of $C_1$–$C_4$aminoalkyl, $C_1$–$C_4$hydroxyalkyl, HOOC—$C_1$–$C_4$alkyl, $C_1$–$C_4$alkyl, $C_1$–$C_4$alkoxy, $C_1$–$C_4$alkylthio, benzyl or benzyloxy.

For the purposes of the present invention, a metal is to be understood as meaning an alkali metal [for example lithium (Li), sodium (Na), potassium (K), rubidium (Rb) and caesium (Cs)], an alkaline earth metal (for example magnesium (Mg), calcium (Ca) and strontium (Sr)) or manganese (Mn), iron (Fe), zinc (Zn) or silver (Ag). Physiologically tolerated salts are to be understood as meaning, in particular, the alkali metal and alkaline earth metal salts, for example sodium, potassium, magnesium and calcium salts. Sodium and potassium ions and their salts are preferred.

As alkyl, the divalent radical $A_1$ can be linear or branched and preferably contains from 1 to 8, more preferably from 1 to 6, particularly preferably from 1 to 4, and in particular 1 or 2, C atoms. Examples are 1,6-, 1,5-, 1,4-, 1,3-, 1,2-, 2,3-, 2,4-, 2,5-, 2,6-, 3,4-, 3,5- or 3,6-hexylene, 1,5-, 1,4-, 1,3-, 1,2-, 2,3-, 2,4-, 2,5-, 3,4- or 3,5-pentylene, 1,4-, 1,3-, 1,2-, 2,3-, 2,4- or 3,4-butylene, 1,3-, 1,2- or 2,3- propylene, 1,2-ethylene and methylene.

$A_1$ is particularly preferably linear and is in particular $C_1$–$C_4$alkylene.

Those substituents for $A_1$ are preferred which occur in natural amino acids, i.e. amino-, hydroxy- and carboxyalkyl, for example.

In a preferred embodiment, the bivalent radicals $A_1$ are derived from natural amino acids with the exception of unprotected cysteine.

In the novel polypeptide, the content of the structural elements I, II and IV can, for example, be from 100 to 0.1 mol %, preferably from 100 to 5.0 mol %, more preferably from 100 to 10 mol %, particularly preferably from 100 to 30 mol %, and in particular from 100 to 50 mol %, in the case of structural elements of the formula (I), from 0 to 99.9 mol %, preferably from 0 to 95 mol %, more preferably from 0 to 90 mol %, particularly preferably from 0 to 70 mol %, and in particular from 0 to 50 mol %, in the case of structural elements of the formula (II), and from 0 to 99.9 mol %, preferably from 0 to 95 mol %, more preferably from 0 to 90 mol %, particularly preferably 0–70 mol %, and in particular from 0 to 50 mol %, in the case of structural elements of the formula (IV).

The content of structural elements of the formula IV which are derived from natural amino acids, with the exception of unprotected cysteine, can, for example, be from 0 to 99.9 mol %, preferably from 0 to 95 mol %, more preferably from 0 to 90 mol %, particularly preferably from 0 to 70 mol %, and in particular from 0 to 50 mol %.

The values in mol % always add up to 100%.

The mean molar mass of the polymer is, for example, at least 2 kDa, preferably 10 kDa, more preferably 20 kDa, particularly preferably 30 kDa, and can be up to 500 kDa, more preferably up to 100 kDa and particularly preferably up to 70 kDa.

The novel polymers may be obtained in a simple manner and, surprisingly, in very high yields and at high purities by reacting polypeptides which contain appropriate functional groups with ester-forming or amide-forming derivatives of haloacetic acids.

The invention furthermore relates to a process for preparing polymers having identical or different structural elements of the formula (I) and, if desired, structural elements of the formulae II and IV,

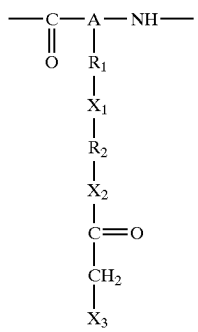

(I), in which A, $R_1$, $X_1$, $R_2$, $X_2$ and $X_3$ are as defined above, which comprises reacting polymers having identical or different structural elements of the formula (II), and, if desired, identical or different structural elements of the formula IV,

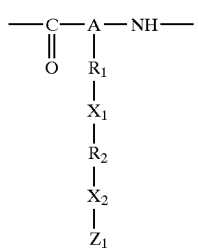

(II), in which
$Z_1$, A, $R_1$, $X_1$, $R_2$ and $X_2$ are as defined above, with an amide-forming or ester-forming derivative of a mono-haloacetic acid in the presence of an acid-capturing agent.

The amide-forming or ester-forming derivative can, for example, be an acid anhydride or acid halide, for example those of the formulae IIIa or IIIb,

(IIIa)

(IIIb), in which $X_3$ is as defined above and $X_4$ is preferably chlorine or bromine; or the derivatives can be activated esters of the formula IIIc,

(IIIc), in which $X_3$ is as defined above and Y is, for example, pentafluorophenyl-, p-nitrophenyl-,

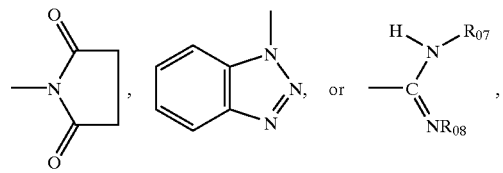

in which $R_{07}$ and $R_{08}$ are cyclohexyl or Isopropyl.

Chloroacetic anhydride is particularly preferably used.

Examples of suitable acid-capturing agents are organic nitrogen bases, in particular tertiary amines having, for example, from 3 to 30, preferably from 3 to 20, and particularly preferably from 3 to 12 C atoms. The tertiary amine is preferably a sterically hindered, non-nucleophilic tertiary amine, preferably a cyclic, sterically hindered, non-nucleophilic tertiary amine. The cyclic amines can be of an aliphatic or aromatic nature and they are substituted in one or both positions which are ortho to the N atom, for example by alkyl groups which contain from 1 to 4 C atoms, for example methyl or ethyl. Aromatic amines which are substituted in both ortho positions are preferred. A particularly preferred example is 2,6-lutidine.

The acid-capturing agent can be present in the reaction mixture stoichiometrically or as a cosolvent.

The reaction temperature is advantageously from −40 to +100° C., preferably from −20 to +70° C., particularly preferably from −10 to +50° C.

The reaction advantageously takes place in the presence of a polar or apolar, aprotic solvent. Preference is given to nitrogen-dialkylated carboximides and lactams, sulfoxide and sulfones, for example dimethylformamide, dimethylacetamide, N-methylpyrrolidone, dimethyl sulfoxide, and tetramethylene sulfone.

The novel polypeptides are outstandingly suitable for preparing, in a specific manner and at exceptionally high purities, polypeptides which contain recognition molecules and which have precisely defined contents, with it additionally being possible to set desired properties such as water-solubility, swellability or water-insolubility in a precise manner. The novel polymers are biologically degradable and therefore particularly suitable for applications in the physiological sphere, with it being possible to match the polymer properties precisely to the existing requirements. The ease of preparation by means of replacing the halogen group $X_3$ with compounds containing thiol groups is particularly worth mentioning.

The invention furthermore relates to polypeptides having identical or different structural elements of the formula (V)

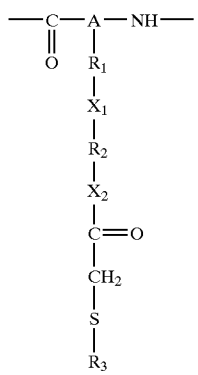
(V), in which A, $R_1$, $X_1$, $R_2$ and $X_2$ are as defined above, and $R_3$ is a biological active group which is covalently bound to the S atom either directly or by way of a bridging group Y.

Biological active group means that there is a receptor function or ligand function or that the swelling or solubility properties in water are affected or that a receptor function or ligand function is combined with the alteration in the swellability or solubility properties. The biological active group consequently has a ligand function, or the active group additionally or only has a swellability or solubility-altering function.

Direct linkage means that the biological active group $R_3$ is bound to a side chain of the polymer by way of an S atom. Bound by way of a bridging group $Y_1$ means that the S atom is bound to a bridging group $Y_1$ and to a side chain of the polymer, with it being possible for the bridging group $Y_1$ to be bound to the biological active group $R_3$ either directly or by way of a functional group.

The bridging group $Y_1$ for $R_3$ can, independently, have the same meanings as the bridging group $R_2$, including the preferences. Preferred examples are $C_1$–$C_{18}$alkylene which is uninterrupted or is interrupted by one or more, preferably one to three, —NH—CO— groups, and, more preferably, $C_1$–$C_2$alkylene, and, particularly preferably, $C_3$–$C_8$alkylene which is not interrupted or is interrupted by an —NH—CO— group. An advantageous bridging group $Y_1$ is oligo- or poly-ethylene glycol.

$R_4$ and $R_6$ are preferably, independently of each other, $C_1$–$C_{12}$alkylene which is unsubstituted or substituted by one or more substituents selected from the group consisting of OH, amino, $C_1$–$C_4$ alkyl, $C_1$–$C_4$ alkoxy or $C_1$–$C_8$ acylamino. $R_4$ and $R_6$ are more preferably, independent of each other, $C_1$–$C_6$ alkylene which is unsubstituted or substituted by one or more substituents selected from the group consisting of OH, amino, $C_1$–$C_4$ alkyl, $C_1$–$C_4$ alkoxy or $C_1$–$C_8$ acylamino. Particularly preferred examples are methylene, ethylene, 1,2- and 1,3-propylene and 1,2-, 1,3- and 1,4-butylene. As arylene, $R_4$ and $R_6$ are preferably phenylene and as aralkylene, $R_4$ and $R_6$ are preferably benzylene.

The novel polypeptides can be homopolymers or copolymers having different biological active groups $R_3$.

In another embodiment, the novel polypeptides can be copolymers which are composed of at least one structural element of the formula (V) and at least one further structural element of the formulae (I), (II) and (IV). The bivalent peptide residues of the natural amino acids, with the exception of unprotected cysteine, are particularly suitable as structural elements of the formula IV.

In a further embodiment, the novel polypeptides contain at least one structural element of the formula (Va)

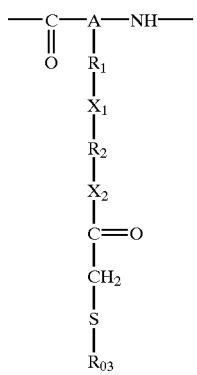
(Va)

in which A, $R_1$, $R_2$, and $X_2$ are as defined above, and $R_{03}$ is a radical of the formula (IX),

(IX)

in which $X_6$ is CO, $SO_2$, P=O, $NR_{11}SO_2$ or O—P=O, in which $R_{11}$ is $C_1$–$C_6$ alkyl or H, or their salts, for example alkali metal, alkaline earth metal or ammonium salts (Na, K, Ca or Mg), or $R_{03}$ is a polyhydroxyalkyl or cycloalkyl radical having preferably from 2 to 12 and particularly preferably from 2 to 6 C atoms and also from 1 to 6 and preferably from 2 to 5 hydroxyl groups, or a copoymer having structural elements of the formula (Va) and at least one of the structural elements of the formulae I, II and IV. The alkylene group in formula (IX) is preferably $C_1$–$C_6$alkylene, particularly preferably $C_1$–$C_4$alkylene.

A preferred subgroup of the novel polypeptides are copolymers having structural elements of the formulae (V) and (Va). The structural elements of the formula V are preferably present in a quantity of from 0.1 to 50, more preferably of from 0.5 to 40, and particularly preferably of from 1 to 20 mol %, and the structural elements of the formula Va are preferably present in a quantity of from 99.9 to 50, more preferably of from 99.5 to 60, and particularly preferably of from 99 to 80 mol %.

The embodiments and preferences which were previously presented for the structural elements of the formulae I, II and IV also apply to the polypeptides having structural elements of the formula V.

The content of the structural elements in the polypeptide can, for example, be from 100 to 0.1 mol %, preferably from 100 to 5.0 mol %, more preferably from 100 to 10 mol %, particularly preferably from 100 to 30 mol %, and in particular from 100 to 50 mol % for structural elements of the formula (V), from 0 to 99.9 mol %, preferably from 0 to 95 mol %, more preferably from 0 to 90 mol %, particularly preferably from 0 to 70 mol % and in particular from 0 to 50 mol % for structural elements of the formula (I), from 0 to 99.9 mol %, preferably from 0 to 95 mol %, more preferably from 0 to 90 mol %, particularly preferably from 0 to 70 mol %, and in particular from 0 to 50 mol %, for structural elements of the formula (II), from 0 to 99.9 mol %, preferably from 0 to 95 mol %, more preferably from 0 to 90 mol %, particularly preferably from 0 to 70 mol %, and in particular from 0 to 50 mol % for structural elements of the formula (IV). The content of natural amino acid residues of the formula (IV), with the exception of unprotected cysteine, can be from 0 to 99.9 mol %, preferably from 0 to 95 mol %, more preferably from 0 to 90 mol %, particularly preferably from 0 to 70 mol %, and in particular from 0 to 50 mol %.

The values in mol % always add up to 100%.

The molecular weight of the polypeptide can, for example, be at least 2 kDa, preferably at least 20 kDa, and it can be up to 500 kDa, more preferably up to 300 kDa and particularly preferably up to 250 kDa.

As a biological active group, $R_3$ is preferably a monovalent or oligovalent ligand which is recognized and bound by a receptor molecule. Preferred ligands are biologically active molecules, for example pharmaceuticals, particularly preferably alkaloids which are highly active pharmacologically; preference is given to biologically active molecules such as carbohydrates, particularly preferably oligosaccharides and polysaccharides, preferably structures or corresponding mimetics as occur on glycoproteins and glycolipids; preference is also given to biologically active molecules such as vitamins, particularly preferably biotin and biotin analogues; preference is also given to biologically active molecules such as peptides and proteins, with active compounds being particularly preferred which have an oligopeptide or polypeptide structure or relatively low molecular weight, in particular active compounds having an oligopeptide or polypeptide structure of relatively low molecular weight which possess a hormonal (peptide hormones), antibiotic (peptide antibiotics) or toxic (peptide toxins) effect; preference is also give to conjugated proteins such as glycoproteins and glycolipids; preference is also given to biologically active molecules such as lipids; preference is also given to biologically active molecules such as terpenes, particularly preferably bitter substances, pheromones, carotinoids, insecticides, cytostatications and antibiotics; preferred ligands are biologically active molecules such as oligonucleotides, particularly preferably RNA and DNA; preference is also given to biologically active molecules such as antigens, more preferably their antigenic determinants and particularly preferably the hapten itself, in particular viral antigens, bacterial antigens, antigens of parasites, viral surface proteins, bacterial surface proteins, surface proteins of parasites, insecticides and toxins; preference is also given to biologically active molecules such as antibodies, particularly preferably immunoglobulins G, M, A and E, more preferably antibodies which are directed against viral antigens, bacterial antigens, antigens of parasites, tumour antigens, viral surface proteins, bacterial surface proteins, oligosaccharide sequences of crosslinked polysaccharides as occur on bacterial cell walls, surface proteins of parasites, insecticides and toxins.

For example, $R_3$ is particularly preferably a monosaccharide, oligosaccharide or polysaccharide residue, for example a carbohydrate residue of the formula $C_n(H_2O)_n$ and also polyhydroxy aldehydes, polyhydroxy ketones, polyhydroxy acids and polyhydroxy amines which are derived therefrom.

The carbohydrate residue can consist of from 1 to 20 naturally occurring sugar monomers and also modified sugar monomers. Use is preferably made of from 1 to 15, and particularly preferably of from 1 to 10, naturally occurring sugar monomers. The skilled person is familiar with naturally occurring sugar monomers from the standard works of organic chemistry or biochemistry, for example from Beyer/Walter, "Lehrbuch der organischen Chemie (Textbook of organic chemistry)", S. Hirzel Verlag Stuttgart, 21st edition, pp. 425ff.; Albert Lehninger, "Biochemie (Biochemistry)", 2nd edition, pp. 201ff., VCH-Verlagsgesellschaft Weinheim, Germany, or Lubert Streyer, "Biochemie (Biochemistry)", Spektrum-der-Wissenschaft Verlagsgesellschaft GmbH, Heidelberg, Germany, 1st edition, pp. 345 ff., and J. F. Kennedy, ed., "Carbohydrate Chemistry", Clarendon Press, Oxford, 1988, pp. 4 ff.).

Examples of sugar monomers are selected from the group consisting of D- and L-aldo-pyranoses and D- and L-aldofuranoses, for example glyceraldehyde, erythrose, threose, ribose, arabinose, xylose, lyxose, allose, altrose, glucose, mannose, gulose, idose, galactose and talose, from the group consisting of D- and L-ketopyranoses and D- and L-ketofuranoses, for example dihydroxyacetone, erythrulose, ribulose, xylulose, psicose, fructose, sorbose and tagatose, and also from the group consisting of D- and L-diketopyranoses, for example pentodiulose and hexodiulose.

The term sugar monomers also includes those sugar monomers which are modifications of the examples listed. The skilled person understands these modifications to include, for example, protected, partially protected or unprotected deoxysugars of the D- and L-configurations, preferably 2-, 3-, 4-, 5- and 6-deoxyaldoses, such as fucose, rhamnose and digitoxose, 1,2-dideoxyaldoses, such as glucal, galactal and fucal, and 1-, 3-, 4-, 5- and 6-deoxyketoses, 2-, 3-, 4-, 5- and 6-deoxyaminosugars of the D and L configurations, such as glucosamine, mannosamine, galactosamine and fucosamine, and deoxyacylaminosugars, such as N-acylglucosamine, N-acylmannosamine, N-acylgalactosamine and N-acyl-fucosamine, preferably their $C_1$–$C_4$alkyl esters.

In addition, these modifications are understood to mean aldonic, aldaric and uronic acids, such as gluconic acid or glucuronic acid, and also ascorbic acid, amino acid-carrying sugar monomers and those which carry lipid, phosphatidyl or polyol residues.

Modified sugar monomers are also understood to mean those having a carbon chain which is longer than 6 C atoms, such as heptoses, octoses, nonoses, heptuloses, octuloses and nonuloses, and also their representatives which are substituted in accordance with the above-listed criteria, such as ketodeoxyoctanic acid, ketodeoxynonanic acid, N-acylneuraminic acids and N-acylmuraminic acids.

Within the scope of the present invention, dimeric and trimeric sugars are understood to mean those which are assembled from two or three of the abovementioned, identical or different, monomers. The linkage is preferably α-O-glycosidic or β-O-glycosidic, with, however, S-, N- and C-glycosidic linkages also coming into consideration. All the C atoms of the one partner of a bond come into consideration. Examples are, in particular, (1→2)-, (1→3)-, (1→4)-, (1→5)-, (1→6)-, (2→3)- and (2→6)-glycosidic linkages. Examples sugars are selected from the group consisting of trehalose, sophorose, kojibiose, laminaribiose, maltose, cellobiose, isomaltose, gentibiose, sucrose and lactose, and their derivatives. Examples of trimeric sugars are raffinose and melezitose.

Examples of particularly preferred embodiments of the carbohydrate moiety are sialyl-Lewis X or sialyl-Lewis A and also analogues of sialyl-Lewis X or sialyl-Lewis A.

$R_3$ is preferably a $C_1$–$C_8$alkyl which is substituted by —$CO_2H$ or —$SO_3H$, or their alkali metal or alkaline earth metal salts. Examples are —$CH_2CH_2SO_3Na$ and —$CH_2$—COONa.

$R_3$ is preferably an oligonucleotide. The oligonucleotide can be partially or completely composed of natural DNA building blocks or unnatural synthetic nucleotides. Synthetic building blocks comprise the modifications of natural building blocks in the nucleic acid base, the furanose ring and/or the bridging groups of the oligonucleotides. In general, synthetic building blocks are employed in order to enhance the complex formation in duplex structures and/or increase the stability of the oligonucleotides towards the degradation which is caused, for example, by nucleases. Within the field of antisense technology, modified nucleosides for synthesizing or modifying complementary oligonucleotides have become known in large numbers and are not therefore discussed here in more detail (see, for example, E. Uhlmann et al., Chemical Reviews, Volume 90, Number 4, pages 543 to 584 (1990)).

Suitable modifications are modifications in the nucleic base part (for example substitutions or omission of substituents), in the nucleotide bridging group (for example modification of the phosphoric ester group or its replacement with other bridging groups) and in the furanose ring (for example substitutions on the 2'-hydroxyl groups, replacement of the furanose O atom, replacement of the furanose ring with monocarbocyclic or bicarbocyclic rings and replacement of the furanose ring with open-chain structures).

The oligonucleotides can, for example, contain from 5 to 100, preferably from 5 to 50, particularly preferably from 8 to 30, and very particularly from 10 to 25, building blocks.

The oligonucleotides are preferably composed of nucleosides from the purine and pyrimidine series. They are particularly preferably composed of 2'-deoxy-2-aminoadenosine, 2'-deoxy-5-methylcytosine, 2'-deoxyadenosine, 2'-deoxycytidine, 2'-desoxycytidine, 2'-deoxy-guanosine and 2'-thymidine. Very particular preference is given to 2'-deoxyadenosine (A), 2'-deoxycytidine (C), 2'-deoxyguanosine (G) and 2'-thymidine (T). Modified building blocks are preferably derived from natural nucleosides of the purine and pyrimidine series, particularly preferably from adenosine, cytidine, guanosine, 2-aminoadenosine, 5-methylcytosine, thymidine and the previously mentioned deoxy derivatives. The nucleosides can be 2'-modified ribonucleosides.

In a very particularly preferred embodiment of the invention, the oligonucleotide is composed of natural deoxynucleosides, particularly preferably from the group 2'-deoxyadenosine (A), 2'-deoxycytidine (C), 2'-deoxyguanosine (G), and 2'-thymidine (T), or of complementary, unnatural synthetic building blocks. Within the scope of the invention, those modified nucleosides are particularly preferred which increase the stability of the oligonucleotide towards nucleases.

The oligonucleotide can also consist of sequences of peptide nucleic acid (PNA). The same preferences as for the oligonucleotides apply for constructing the PNA sequence. Examples of PNA's are to be found in Science, Volume 254, pages 1497 to 1500.

The oligonucleotide can be partially or completely composed of natural DNA building blocks which are complementary to the target RNA or target DNA or be completely composed of unnatural synthetic nucleotides which are likewise complementary to the target RNA or target DNA, with partially meaning that natural DNA building blocks which are complementary to the target RNA are replaced in the oligonucleotide sequence with unnatural synthetic nucleotides which are likewise complementary.

Within the scope of the present invention, target RNA means that an RNA sequence must be present in the target. Accordingly, polyribonucleic acids (RNA) can be present. This RNA is preferably mRNA (messenger RNA), pre-mRNA (precursor mRNA), tRNA (transfer RNA), snRNA (small nuclear RNA), rRNA (ribosomal RNA) and viral RNA. However, mixed sequences of RNA and polydeoxyribonucleic acids (DNA) can also be present, for example the RNA-DNA chimeras (Okazaki fragments). The RNA possesses sufficient building blocks to allow a complex (double strand) to be formed with the oligonucleotide. Within the scope of the present invention, target DNA means that a complementary DNA sequence must be present in the target. The DNA possesses sufficient building blocks to allow a complex (double strand) to be formed with the oligonucleotide.

The choice and the order of the building blocks in a sequence of oligonucleotide is determined by the necessary formation of a duplex with a target RNA or target DNA.

The number of the building blocks in the oligonucleotide is calculated to ensure that hybridization takes place with the target RNA or target DNA. The regions (pairing nucleotide building blocks) which increase pair formation with the target RNA or target DNA are preferably arranged in the more central sequences of the oligonucleotide, for example between in each case the fourth last, or in each case the third last, or in each case the second last, or in each case the last, building blocks of the sequence. In an oligonucleotide having, for example, 20 building blocks, pairing building blocks are preferably located in the region from the fourth to the seventeenth building block.

In a particular embodiment, $R_3$, as a biological active group, is preferably a sugar molecule or its derivative; more preferably, $R_3$ is a sugar molecule residue of a glycolipid, glycoprotein or polysaccharide; particularly preferably, $R_3$ is N-acetylglucosamine or its derivatives, glucose or its derivatives, lactose or its derivatives, sialyl-Lewis x or its derivatives, or sialyl-Lewis a. As a biological active group, $R_3$ is preferably biotin.

The invention additionally relates to a process for preparing polypeptides from at least one structural element of the formula V or at least two different structural elements of the formula (V) and, if desired, structural elements of the formulae I, II and IV,

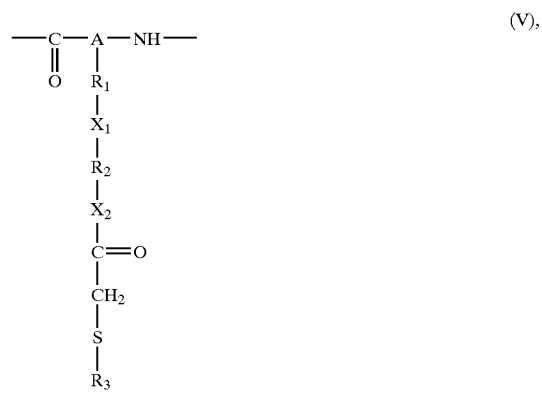

in which A, $R_1$, $X_1$, $R_2$, $X_2$ and $R_3$ are as defined above, which comprises reacting polypeptides having structural elements of the formula I, and, if desired, structural elements of the formulae II and/or IV,

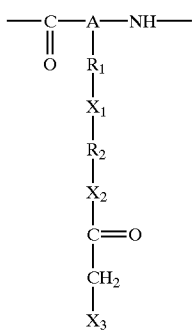

(I)

in which A, $R_1$, $X_1$, $R_2$, $X_2$ and $X_3$ are as defined above, with a thiol of the formula VIII, $$R_3—SH \qquad (VIII)$$

in which $R_3$ is as defined above, in the presence of a strong, non-nucleophilic base having at least one tertiary N atom.

The thiols are either known or can be prepared by methods which are known per se. It is particularly advantageous to introduce the thiol group by reacting compounds of the formula $R_3YH$ with thiolactones, with —YH being a functional group, for example —OH or $NH_2$.

Suitable and preferred bases are bicyclic or polycyclic amines having at least one tertiary N atom. Examples are quinuclidine and 1,8-diazabicyclo[5.4.0]undec-7-ene(1,5-5) (DBU).

The base is employed in at least equimolar quantities, preferably in slight excesses.

It has been found, surprisingly, that it is possible to achieve quantitative reactions and high purities so that the polypeptides can be used directly without further elaborate purifications, even in the biological sphere. The reaction can also be carried out using alkali metal thiolates $R_3SM$ (M is alkali metal)

The reaction can be effected in the presence of a polar, aprotic solvent. Those which are preferred are nitrogen-dialkyiated carboxyimides and lactams, sulfoxides and sulfones, for example dimethylformamide, dimethylacetamide, N-methylpyrrolidone, dimethyl sulfoxide and tetramethylene sulfone.

The reaction can be effected either with or without the addition of water, for example up to quantities at which the polymer remains in solution.

The temperature range in which the reaction can be effected extends, for example, from 0 to 200° C., preferably from 0 to 150° C., particularly preferably from 20 to 100° C. and in particular from 20 to 50° C.

The invention furthermore relates to the novel compounds for use in a therapeutic method for treating diseases in homoiothermic animals, including man. The dosage when administering to homoiotherms of about 70 kg bodyweight can, for example, be from 0.01 to 1000 mg per day. Administration is preferably effected parenterally, for example intravenously or intraperitoneally, in the form of pharmaceutical preparations.

The compounds according to the invention have antiinflammatory properties and can accordingly be used as medicaments. It is possible with them in particular to alleviate disorders such as cardiogenic shock, myocardial infarct, thrombosis, rheumatism, psoriasis, dermatitis, acute respiratory distress syndrome, asthma, arthritis and metastatic cancer.

The invention furthermore relates to a pharmaceutical preparation which comprises an effective quantity of the novel compound, either alone or together with other active ingredients, a pharmaceutical carrier, preferably in a significant quantity, and adjuncts, if desired.

The pharmacologically active, novel compounds can be used in the form of parenterally administerable preparations or infusion solutions. These solutions are preferably isotonic, aqueous solutions or suspensions, with it being possible, for example in the case of lyophilized preparations, which comprise the active substance either alone or together with a carrier, for example mannitol, to prepare the latter prior to use. The pharmaceutical preparations can be sterilized and/or comprise adjuncts, for example preservatives, stabilizers, wetting agents, emulsifiers, solubilizers, salts for regulating the osmotic pressure and/or buffers. The pharmaceutical preparations, which, if desired, can also comprise additional pharmacologically active substances, for example antibiotics, are prepared in a manner known per se, for example using conventional solubilizing or lyophilizing methods, and comprise from about 0.1% to 90%, in particular from about 0.5% to about 30%, for example from 1% to 5%, of active ingredient(s).

The polypeptid polymer according to the invention can be used to detect diseases in homeothermic animals including man.

The invention is further directed to a method of using of a polypeptid polymer according to the invention for production of monoclonal antibodies.

The polypeptid polymer according to the invention can be used in a ligand binding assay, preferably for determining the concentration of a compound required to inhibit maximal binding of the polypeptide polymer according to the invention to an immobilized receptor molecule. The immobilized receptor molecule can, according to example D1 of the specification, be an immobilized E-selectin/human lgG chimera or can according to example D2 be an immobilized P-selectin/human IgG chimera.

The linear polymers, which present ligands in a multivalent form, may be employed in the medical sphere as pharmaceuticals for therapy, both in animals and in human medicine.

The effect of the pharmaceuticals is amplified by the multivalent presentation. Alkaloids, vitamins, hormones, antibiotics, toxins and cytostatic agents, for example, can be administered as pharmaceuticals, bound to the linear polymers. The antigens which are bound to the linear polymers can be used as vaccines and can be employed as conjugates with the polymer for active immunization in animals or humans. The conjugates may likewise be employed for preparing monoclonal antibodies against the given hapten structures.

The linear polymers which present ligands in multivalent form can be used, as water-soluble, synthetic polymers, as an artificial replacement for plasma.

Ligands which are selectively recognized by particular receptors can be bound to the linear polymers and selectively direct pharmaceuticals, which are also present, to their sites of action (drug targeting).

The polypeptide according to the invention wherein the biological active group $R_3$ is a ligand which is selectively recognized by a particular receptor can be used to target molecules to their side of action by attaching said molecules to the polypeptide polymer and binding the so modified polypeptide polymer to its particular receptor such that the receptor and the target molecule are in close proximity. The molecules which are targeted can be selected from a group consisting of drugs, genes, biological active proteins and fluorescent polymer coated beads.

The polypeptide according to the invention can be used to select cells, wherein the biological active group $R_3$ is a ligand for proteins or receptors expressed on the selected cell type.

The polypeptide according to the invention can be used in a method for selecting cells by using a polypeptide according to the invention, wherein the biological group $R_3$ is a ligand for proteins or receptors expressed on the selected cell type. The method for selecting cells can be selected from a group consisting of panning on immobilized polypeptides, cell chromatographie or fluorescence activated cell sorting.

The polypeptide according to the invention can be used to inhibit binding of cells type A to cells of type B, wherein the biological active group $R_3$ is an inhibitor which upon incubation of cells of type A or upon incubation of cells of type B or incubation of both prevents binding of cells of type A with specific ligands bound to their surface to a particular receptor expressed on cells of type B.

The polypeptide according to the invention can preferably be used to inhibit binding of polymorphonuclear leukocytes (PMNs) with Sialyl Lewis x groups bound to their surface, to Human Umbilical Vein Endothelial cells (HUVECS) which upon stimulation with Tumor Necrosis Factor a (TNF) express E-selectin on their surface.

The polypeptide according to the invention can be used to study the rolling behavior of cells of type A on the confluent layer of cells of type B, which is a characteristic of cells of type A in contact with a receptor expressed on cells of type B in presence of hydrodynamic flow. According to Example D3 the cells of type A are preferably polymorphonuclear leukocytes (PMNs) with Sialyl Lewis x groups bound to their surface, and cells of type B are preferably Human Umbilical Vein Endothelial cells (HUVECS) which upon stimulation with Tumor Necrosis Factor a (TNF) express E-selectin on their surface The present invention is further directed to a composition for determining the concentration of a compound required to inhibit maximal binding of a polypeptide polymer according to the invention to an immobilized receptor molecule in form of a ready-to-use test kit, comprising in addition to the carrier materials, reagents and other additives customarily used at least one polypeptide polymer according to the invention. The ready-to-use test kit preferably comprises a carrier which is compartementalized so as to receive, in close mutual confinement therein:
  a) a solid support having affixed thereto the receptor molecule capable of reacting with the polypeptide polymer according to claim 25 and
  b) a detecting system for a binary complex. The present invention is preferably directed to a composition used according to Examples D1 and D2.

The present invention is further directed to a composition for quantification of the rolling behavior of the cells of type A in the presence of a hydrodynamic flow on the confluent layer of cells B in form of a ready-to-use test kit, comprising in addition to the carrier materials, reagents and other additives customarily used at least one polypeptide polymer according to the invention.

The polypeptid polymer according to the invention can be used for immunization in animals or humans, wherein the antigens are bound to the linear polymers.

Under defined physiological conditions, pharmaceuticals which are bound to the linear polymers by way of labile bonds can either be released over a very long period (slow release) or at specific sites of action (controlled release). This is particularly effective in the case of combination preparations.

Polymeric compounds which present ligands in multivalent form may be employed as receptor blockers, for example, in ligand-receptor recognition processes.

The present invention is preferably directed to a composition used according to Examples D3.

The ligands which are bound to the linear polymers are presented in multivalent form by the recurring structural elements of the polymer. These polymers are particularly valuable when used as the recognition component in an analytical test system.

In the sphere of medical diagnosis, the linear polymers which present ligands in multivalent form can be used in an immunoassay for the early recognition of diseases by detecting specific indicator substances, for example in the diagnosis of cancer or for diagnosing viral or bacterial diseases or for diagnosing parasite infestation. In this context, the recognition component can be immobilized antibodies for detecting specific antigens or immobilized antigens for detecting specific antibodies. The immobilized antigen can, for example, be a surface protein of the HIV virus and consequently be used for diagnosing HIV infections.

In the field of analytical environmental diagnosis, immobilized antibodies can be employed, in an immunoassay, as a probe for antigens and consequently be used, for example, for detecting plant protectants, such as atrazine.

In the field of medical diagnosis, immobilized oligonucleotides can be employed, in a test system, as a probe for target oligonucleotide sequences, for genomic analysis, or for diagnosing genetically determined diseases, such as cystic fibrosis.

In sensor technology, the linear polymers which present ligands in multivalent form can be included, as recognition elements, in the active layer, both in optical and in electrochemical sensors, with it being possible for the recognition element to be an antibody, an antigen or an oligonucleotide which is immobilized on the sensor surface. Examples of the recognition element correspond to the abovementioned examples in the fields of medical or environmental diagnosis.

Insecticides which are bound to the linear polymers can be employed for controlling insects.

The following examples clarify the invention. In the examples which follow, the following abbreviations are used:

Ac:       acetyl
Bn:       Benzyl
GlcNAc:   N-acetylglucosamine
GPC:      gel permeation chromatography
HRP:      Horse-radish Peroxidase
HUVECS:   Human Umbilical Vein Endothelial Cells Lac:

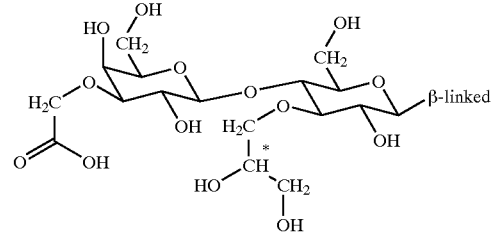

MALLS:    medium-angle laser light scattering
$\overline{M}_w$:       average molecular weight -continued

| n: | degree of polymerization |
|---|---|
| PMN: | polymorphous neutrophiles |
| RBC: | red blood cells |
| sLex: | sialyl-Lewis x |
| sLea: | sialyl-Lewis a |
| SA: | streptavidin |
| TMP: | 3,3',5,5'-tetramethylbenzidine |
| TNF: | tumor necrosis factor |
| Z: | Benzyloxycarbonyl |

The $\overline{M}_w$ of the polylysine hydrobromides which are commercially obtainable from SIGMA were determined by means of viscosity measurements and SEC-LALLS (size exclusion chromatography/low angle laser light scattering) of the succinyl derivatives of the compounds.

A: PREPARATION OF STARTING COMPOUNDS a) Preparation of Compounds Analogous to Formula (VIII)

EXAMPLE A1

Reaction of Propylamine-β-N-acetylqlucosaminodyranoside With γ-Thiobutyrolactone

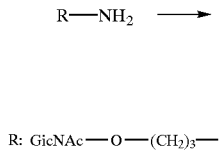

R: GicNAc—O—(CH₂)₃—

500 mg (1.80 mmol) propylamino-β-N-acetylglucosaminopyranoside are dissolved in 15 ml of absolute, oxygen-free methanol. 1840 mg (18.0 mmol) of γ-thiobutyrolactone and 1820 mg (18.0 mmol) of triethylamine are added. The solution is heated under reflux and under argon for 16 h. The solvent is then removed in vacuo and the crude product is purified by flash chromatography (silica gel; ethyl acetate/methanol 3:1). 610 mg (89%) of a colourless solid are obtained.

$^1$H-NMR (CD$_3$OD, 250 MHz) δ=4.36 (1H, d, 8.5 Hz, H$_1$); 3.95–3.15 (10H, m, H2–H6 and —O—C$\underline{H}_2$—CH$_2$—C$\underline{H}_2$—NH—); 2.51 (2H, t, 7.0 Hz, —NH—CO—CH$_2$—CH$_2$—C$\underline{H}_2$—SH); 2.33 (2H, t, —NH—CO—C$\underline{H}_2$—CH$_2$—CH$_2$—SH—); 1.99 (3H, s, CO—C$\underline{H}_3$); 1.88 (2H, quint, 7.0 Hz, —NH—CO—CH$_2$—C$\underline{H}_2$—CH$_2$—SH); 1.72 (2H, m, —O—CH$_2$—C$\underline{H}_2$—CH$_2$—NH—); $^{13}$C-NMR (CD$_3$OD, 72.5 MHz) δ=175.4 (q), 174.9 (q), 102.8 (t), 78.0 (t), 76.1 (t), 72.1 (t), 68.2 (s), 62.8 (s), 57.3 (t), 37.6 (s), 35.6 (s), 31.2 (s), 30.4 (s), 24.5 (s), 23.0 (p).

EXAMPLE A2

Reaction of the Propylamino-β-glycoside of Sialyl-Lewis x With γ-Thiobutyrolactone

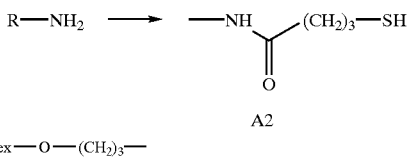

R: sLex—O—(CH₂)₃—

48 mg (0.055 mmol) of propylamino-β-sialyl-Lewis x are dissolved in 4 ml of absolute, oxygen-free methanol. 56 mg (0.55 mmol) of γ-thiobutyrolactone and 55 mg (0.55 mmol) of triethylamine are added. The solution is heated under reflux and under argon for 16 h. The solvent is then removed in vacuo and the crude product is purified by flash chromatography (silica gel; chloroform/methanol/water 55:45:10). 38 mg (64%) of a colourless solid are obtained.

hu 1H-NMR (D$_2$O, 500 MHz), selected signals δ=5.05 (1H, d, 4.0 Hz, Fuc-H$_1$); 4.46 (2H, d, 8.0 Hz, Gal-H$_1$ und GlcNAc-H$_1$); 4.03 (1H, dd, 10.0/3.0 Hz); 3.96 (1H, dd, 12.0/1.5 Hz); 2.71 (1H, dd, 12.0/4.0 Hz, Sia-H$_{3a}$); 2.48 (2H, t, 7.0 Hz, —NH—CO—CH$_2$—CH$_2$—C$\underline{H}_2$—SH); 2.30 (2H, t, —NH—CO—C$\underline{H}_2$—CH$_2$—CH$_2$—SH—); 1.97 (6H, s, 2×CO—C$\underline{H}_3$); 1.83 (2H, quint, 7.5 Hz, —NH—CO—CH$_2$—C$\underline{H}_2$—CH$_2$—SH); 1.76 (1H, t, 12.0 Hz, Sia-H$_{3b}$); 1.70 (2H, quint, 6.0 Hz, —O—CH$_2$—C$\underline{H}_2$—CH$_2$—NH—); MS (MALDI-TOF): 979 (M$^+$).

EXAMPLE A3

Reaction of (N-Biotinyl) hexamethylenediaminetrifluoroacetate With γ-Thiobutyrolactone

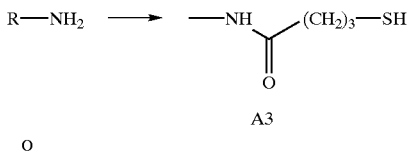

R: 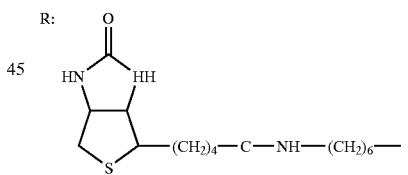

80 mg (0.175 mmol) of (N-biotinyl)hexamethylenediaminetrifluoroacetate are dissolved in 3 ml of absolute, oxygen-free methanol. After 600 mg of Amberlite IRA 910 ion exchange resin have been added, the mixture is stirred at room temperature for 1 h. After filtering, the solvent is removed in vacuo and the residue is taken up in 7.5 ml of oxygen-free methanol. 18 mg (0.175 mmol) of γ-thiobutyrolactone and 18 mg (0.175 mmol) of triethylamine are added. The solution is heated under reflux and under argon for 16 h. The solvent is then removed in vacuo and the crude product is purified by flash chromatography (silica gel; chloroform/methanol 91:9). 48 mg (61%) of a colourless solid are obtained.

$^1$H-NMR (CD$_3$OD, 250 MHz), selected signals δ=4.39 (1H, dd, 8.0/5.0 Hz), 4.20 (1H, dd, 8.0/4.5 Hz), 2.83 (1H, dd, 12.0/5.0 Hz), 2.59 (1H, d, 12.0 Hz), 2.39 (2H, t, 7.0 Hz), 2.20 (2H, t, 7.0 Hz), 2.09 (2H, t, 7.0 Hz), 1.77 (2H, quint, 7.0 Hz); $^{13}$H-NMR (CD$_3$OD, 72.5 MHz) δ=176.6 (q), 176.0 (q), 175.3 (q), 63.4 (t), 61.6 (t), 57.1 (t), 41.1 (s), 40.3 (2C, s), 36.8 (s), 35.6 (s), 31.4 (s), 30.4 (2C, s), 29.8 (s), 29.5 (s), 27.6 (2C, s), 27.0 (s), 24.5 (s).

EXAMPLE A4

Reaction of the Lactose Derivative with γ-Thiobutyrolactone

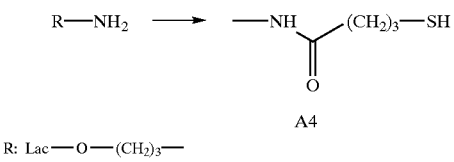

R: Lac—O—(CH$_2$)$_3$—

25 mg (0.047 mmol) of lactose derivative are dissolved in 3.5 ml of absolute, oxygen-free methanol. 40 mg (0.47 mmol) of γ-thiobutyrolactone and 47 mg (0.47 mmol) of triethylamine are added. The solution is heated under reflux and under argon for 16 h. The solvent is then removed in vacuo and the crude product is purified by flash chromatography (silica gel; chloroform/methanol/water 30:30:8). 21 mg (70%) of a colourless solid are obtained.

$^1$H-NMR (D$_2$O, 400 MHz), selected signals δ=4.45 und 4.44 (2H, 2×d, 8.0 Hz, Gal-H$_1$ and GlcNAc-H$_1$); 4.05 (3H, m); 3.98–3.85 (4H, m); 2.70 (2H, t, 7.0 Hz, —NH—CO—CH$_2$—CH$_2$—CH$_2$—SH); 2.50 (2H, t, 7.0 Hz, —NH—CO—CH$_2$—CH$_2$—CH$_2$—SH—); 1.83 (2H, m, —NH—CO—CH$_2$—CH$_2$—CH$_2$—SH); 1.70 (2H, quint, 7.0 Hz, —O—CH$_2$—CH$_2$—CH$_2$—NH—); MS (EI): 656 (M+Na)$^+$.

EXAMPLE A5

Reaction of the Propylamino-β-glycoside of Sialyl-Lewis a With γ-Thiobutyrolactone

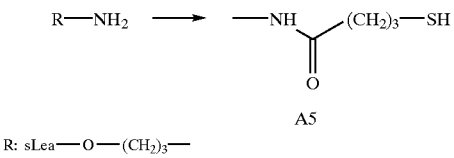

R: sLea—O—(CH$_2$)$_3$—

88 mg (0.032 mmol) of propylamino-β-sialyl-Lewis a are dissolved in 4 ml of absolute, oxygen-free methanol. 33 mg (0.32 mmol) of γ-thiobutyrolactone and 33 mg (0.32 mmol) of triethylamine are added. The solution is heated under reflux and under argon for 16 h. The solvent is then removed in vacuo and the crude product is purified by flash chromatography (silica gel; chloroform/methanol/water 55:45:10). 23 mg (44%) of a colourless solid are obtained.

$^1$H-NMR (D$_2$O, 500 MHz), selected signals δ=4.96 (1H, d, 4.0 Hz, Fuc-H$_1$); 4.82 (1H q, 6.5 Hz, Fuc-H$_5$); 4.49 (1H, d, 8.0 Hz, GlcNAc-H$_1$); 4.47 (1H, d, 8.0 Hz, Gal-H$_1$); 2.72 (1H, dd, 12.0/4.0 Hz, Sia-H$_{3a}$); 2.49 (2H, t, 7.0 Hz, —NH—CO—CH$_2$—CH$_2$—CH$_2$—S—); 2.30 (2H, t, —NH—CO—CH$_2$—CH$_2$—CH$_2$—S—); 2.00 (3H, s, CO—CH$_3$); 1.99 (3H, s, CO—CH$_3$); 1.83 (2H, quint, 7.5 Hz, —NH—CO—CH$_2$—CH$_2$—CH$_2$—S—); 1.72 (2H, quint, 6.0 Hz, —O—CH$_2$—CH$_2$—CH$_2$—NH—); 1.11 (3H, d, 6.5 Hz, Fuc-H$_6$; MS/EI: 1002 (M+Na)$^+$.

B: PREPARATION OF POLYMERS HAVING IDENTICAL OR DIFFERENT STRUCTURAL ELEMENTS OF THE FORMULA (I)

a) Synthesis of Activated Polylysine Derivatives Having a Molecular Weight $\overline{M}_w$: 30,000–70,000

EXAMPLE B1

Synthesis of N(6)-Chloroacetyl-poly-L-lysine B1

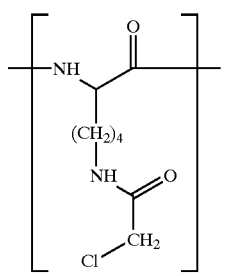

500 mg (2.39 mmol) of poly-L-lysine hydrobromide (SIGMA; M: 30,000–70,000) are suspended in 8 ml of dimethylformamide under argon. The suspension is cooled down to 0° C. and 2.5 ml of 2,6-lutidine are added. A solution of 1000 mg (5.85 mmol) of chloroacetic anhydride in 4 ml of dimethylformamide is added dropwise over the space of 15 min. The mixture is subsequently heated slowly to room temperature and stirred for 5 h. The faintly yellow, slightly turbid solution is added dropwise to 100 ml of diethyl ether/ethanol (2:1) with the formation of a colourless precipitate. Following filtration (through a sintered-glass filter initially without applying a vacuum) washing takes place with ethanol, water, with ethanol again and finally with diethylether. The crude product is dissolved in as little dimethylformamide as possible and precipitated once again in diethyl ether/ethanol. After drying in vacuo at room temperature, 450 mg (92%) of N(6)-chloroacetyl-poly-L-lysine B1 are obtained.

$^1$H-NMR (DMSO, 500 MHz) δ=8.20 (2H, s, 2×NH); 4.05 (2H, s, —CO—CH$_2$—Cl); 3.80 (1H, s, CH); 3.05 (2H, s, —CH$_2$—NH—CO—); 2.00–1.20 (6H, m, —CH—CH$_2$—CH$_2$—CH$_2$—CH$_2$—NH—).

EXAMPLE B2

Synthesis of N(6)-Chloroacetyl-poly-D-lysine B2

In analogy with the reaction of poly-L-lysine hydrobromide (SIGMA; M: 30,000–70,000), 95 mg (95%) of N(6)-chloroacetyl-poly-D-lysine B2 are obtained from 100 mg (0.48 mmol) of poly-D-lysine hydrobromide (SIGMA; M: 30,000–70,000). The $^1$H spectrum is identical to that of compound B1.

EXAMPLE B3

Synthesis of N(6)-Chloroacetyl-poly-D/L-lysine B3

250 mg (1.19 mmol) of poly-D/L-lysine hydrobromide (SIGMA; M: 30,000–70,000) are suspended in 4 ml of dimethylformamide under argon. The suspension is cooled down to 0° C. and 1.25 ml of 2,6-lutidine are added. A solution of 500 mg (2.93 mmol) of chloroacetic anhydride in 2 ml of dimethylformamide is added dropwise over the space of 15 min. The mixture is subsequently heated slowly to room temperature and stirred for 16 h. The working-up and purification take place in analogy with N(6)-chloroacetyl-poly-L-lysine. 210 mg (85%) of N(6)-chloroacetyl-poly-D/L-lysine B3 are obtained.

$^1$H-NMR (DMSO, 500 MHz) δ=8.20 (1H, s, N(6)H); 8.05 and 7.90 (in each case 1/2H, 2s, N(2)H); 4.25 (1 H, s (br), CH); 4.05 (2H, s, —CO—CH$_2$—Cl); 3.05 (2H, s, —CH$_2$—NH—CO—); 1.70 –1.20 (6H, m, —CH—CH$_2$—CH$_2$—CH$_2$—NH—).

EXAMPLE B4

Synthesis of N(6)-Bromoacetyl-poly-L-lysine B4

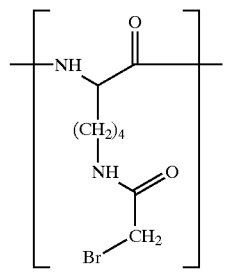

B4

25 mg (0.12 mmol) of poly-L-lysine hydrobromide (SIGMA; M: 30,000–70,000) are suspended in 1 ml of dimethylformamide under argon. The suspension is cooled down to –15° C. and 0.5 ml of 2,6-lutidine is added. A solution of 94 mg (0.36 mmol) of bromoacetic anhydride in 1 ml of dimethylformamide is added dropwise over the space of 60 min. The mixture is subsequently stirred at –10° C. for 2 h. The faintly yellow, slightly turbid solution is added dropwise to 50 ml of diethyl ether/ethanol (2:1), with a colourless precipitate being formed. Following filtration (through a sintered-glass filter initially without applying a vacuum), washing takes place with ethanol, water, once again with ethanol and finally with diethyl ether. The crude product is dissolved in as little dimethylformamide as possible and precipitated once again in diethyl ether/ethanol. After drying in vacuo at room temperature, 25 mg (84%) of N(6)-bromoacetyl-poly-L-lysine B4 are obtained. $^1$ H-NMR (DMSO, 500 MHz) δ=8.25 (2H, s, 2×NH); 3.80 (3H, s, —CO—CH$_2$—Br, CH); 3.05 (2H, s, —CH$_2$—NH—CO—); 2.00–1.20 (6H, m, —CH—CH$_2$—CH$_2$—CH$_2$—NH—).

b) Synthesis of Activated Polylysine Derivatives Having a Molecular Weight $\overline{M}_w$:4,000–15,000

EXAMPLE B5

Synthesis of N(6)-Chloroacetyl-poly-L-lysine

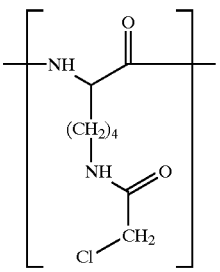

B5

In an analogous manner to the reaction of poly-L-lysine hydrobromide (SIGMA; $\overline{M}_w$:30,000–70,000), 38 mg (77%) of N(6)-chloroacetyl-poly-L-lysine B5 are obtained from 50 mg (0.24 mmol) of poly-L-lysine hydrobromide (SIGMA; $\overline{M}_w$:4,000–15,000). The $^1$H NMR spectrum is identical to that of compound B1.

c) Synthesis of Activated Polylysine Derivatives Having a Molecular Weight $\overline{M}_w$ of 150,000–300,000

EXAMPLE B6

Synthesis of N(6)-Chloroacetyl-poly-L-lysine

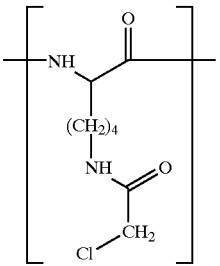

B6

In an analogous manner to the reaction of poly-L-lysine hydrobromide (SIGMA; $\overline{M}_w$:30,000–70,000), 42 mg (85%) of N(6)-chloroacetyl-poly-L-lysine B6 are obtained from 50 mg (0.24 mmol) of poly-L-lysine hydrobromide (SIGMA; $\overline{M}_w$:150,000–300,000). The $^1$H NMR spectrum is identical to that of compound B1.

d) Synthesis of the Chloroacetic Ester of Poly-(hydroxyethyl)-D/L-aspartamide $\overline{M}_m$:40,000; the Degree of Polymerization n is Approximately 250

EXAMPLE B7

Reaction of Poly-(hydroxyethyl)-D/L-aspartamide With Chloroacetic Anhydride

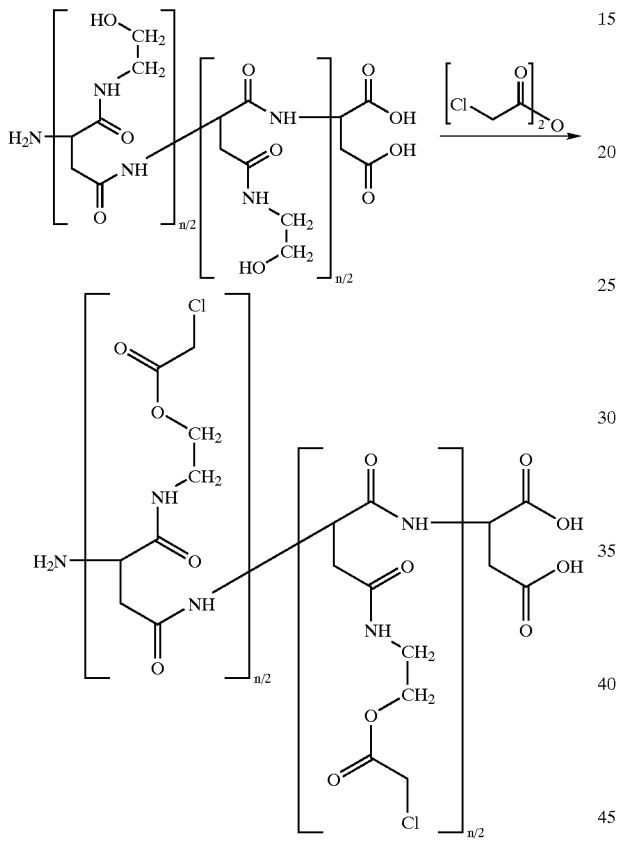

190 mg (1.20 mmol) of Poly-(hydroxyethyl)-D/L-aspartamide (M: 40,000) are dissolved in 5 ml of dimethylformamide under argon. The mixture is cooled down to 0° C. and 1 ml of 2,6-lutidine is added. A solution of 616 mg (3.60 mmol) of chloroacetic anhydride in 2 ml of dimethylformamide is added dropwise over the space of 15 min. The mixture is subsequently heated slowly to room temperature and stirred for 5 h. The faintly yellow solution is added dropwise to 50 ml of diethyl ether/ethanol (2:1), with a colourless precipitate being formed. Following filtration, washing takes place with ethanol, water, with ethanol once again and finally with diethyl ether. The crude product is dissolved in as little dimethylformamide as possible and precipitated once again in diethyl ether/ethanol. After drying in vacuo at room temperature, 210 mg (75%) of the activated polyaspartamide derivative B7 are obtained. $^1$H-NMR (DMSO, 500 MHz) δ=8.33–7.90 (2H, m, N$\underline{H}$); 4.55 (1H, m, C$\underline{H}$); 4.35 (2H, 2×s, —NH—CH$_2$—CH$_2$—O—CO—C$\underline{H}_2$—Cl); 4.10 (2H, m, —NH—CH$_2$—C$\underline{H}_2$—O—CO—CH$_2$—Cl); 3.16 (2H, m, —NH—C$\underline{H}_2$—CH$_2$—O—CO—CH$_2$—Cl); 2.78–2.25 (2H, m, —CH—C$\underline{H}_2$—).

C: PREPARATION OF POLYMERS HAVING IDENTICAL OR DIFFERENT STRUCTURAL ELEMEMTS OF THE FORMULA (V)

a) Synthesis of Water-soluble Polylysine Derivatives by Reaction With Mercaptopolyalcohols

EXAMPLE C1

Reaction of N(6)-Chloroacetyl-poly-L-lysine B1 With Thioalycerol

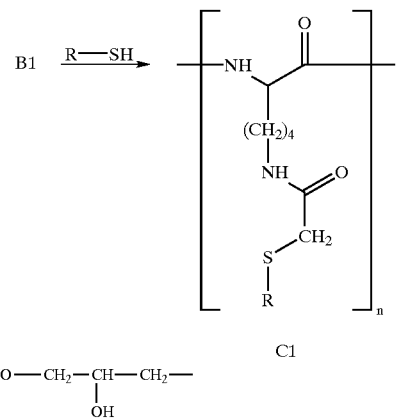

10 mg (0.049 mmol) of N(6)-chloroacetyl-poly-L-lysine are dissolved in 0.5 ml of oxygen-free dimethylformamide at room temperature and under argon. 120 mg (1.1 mmol) of thioglycerol and 40 mg (0.4 mmol) of distilled triethylamine are added. After having been stirred at room temperature for 16 h, the clear, colourless solution is added dropwise to 10 ml of diethyl ether/ethanol (1:1). The precipitate which has formed is filtered off and washed with ethanol. It is then dissolved in water and this solution is lyophilized. 10 mg of colourless product C1 are obtained. The content of thioglycerol is 100 mol % (determined by $^1$H NMR spectroscopy). The yield is 83%. The degree of polymerization n is approximately 250.

$^1$H-NMR (D$_2$O, 500 MHz) δ=4.02 (1H, s (br), C$\underline{H}$); 3.80 (1H, m, —S—CH$_2$—C$\underline{H}$(OH)—CH$_2$—OH); 3.59, 3.53 (je 1H, 2×dd, 12.0, 3.5/12.0, 6.0 Hz, —S—CH$_2$—CH(OH)—C$\underline{H}_2$—OH); 3.27 (2H, s, —NH—CO—C$\underline{H}_2$—S—); 3.18 (2H, s (br), —C$\underline{H}_2$—NH—CO—); 2.74, 2.60 (in each case 1H, 2×dd, 13.5, 4.5/13.5, 7.5 Hz, —S—CH$_2$—CH(OH)—CH$_2$—OH); 2.05–1.35 (6H, —CH—C$\underline{H}_2$—C$\underline{H}_2$—CH$_2$—CH$_2$—NH—). $\overline{M}_w$ (GPC/MALLS): 60,000 D.

EXAMPLE C2

Reaction of N(6)-Chloroacetyl-poly-L-lysine B1
With α/β-Thioglucose

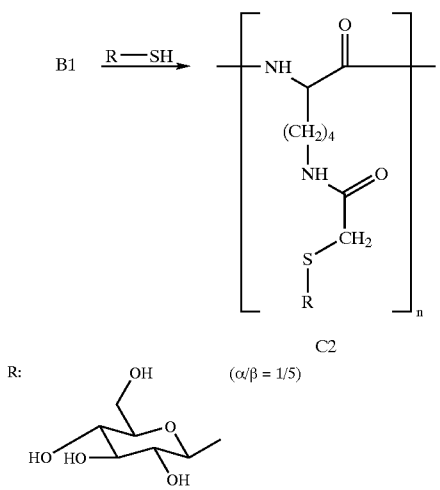

10 mg (0.05 mmol) of N(6)-chloroacetyl-poly-L-lysine are dissolved in 0.5 ml of oxygen-free dimethylformamide at room temperature and under argon. 19 mg (0.1 mmol) of 1-thioglucose (α/β=15:85) and 10 mg (0.1 mmol) of distilled triethylamine are added. After having been stirred at room temperature for 16 h, the faintly grey solution is added dropwise to 10 ml of diethyl ether/ethanol (1:1). The precipitate which has formed is filtered off and washed with ethanol. It is then dissolved in water and this solution is lyophilized. 15 mg of colourless product C2 are obtained. The content of carbohydrate is 100 mol % (determined by $^1$H NMR spectroscopy). The yield is 83%. The degree of polymerization n is approximately 250.

$^1$H-NMR (D$_2$O, 500 MHz) δ=5.40 (15/100H, d, 5.5 Hz, α-H$_1$); 4.50 (85/100H, d, 9.50 Hz, β-H$_1$); 4.05 (1H, s (br), C$\underline{H}$); 3.93–3.20 (6H, m, H$_2$–H$_6$); 3.35 (2H, s, —NH—CO—C$\underline{H}_2$—S—); 3.15 (2H, s (br), —C$\underline{H}_2$—NH—CO—); 2.05–1.35 (6H, —CH—C$\underline{H}_2$—C$\underline{H}_2$—C$\underline{H}_2$—CH$_2$—NH—).

EXAMPLE C3

Reaction of N(6)-Chloroacetyl-poly-L-lysine B1
With "N-Acetyl-glucosaminothiol" A1

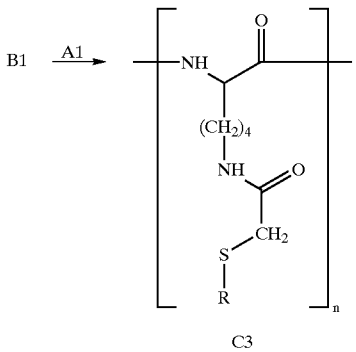

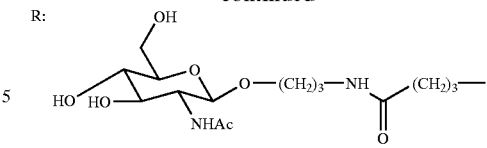

10.0 mg (0.049 mmol) of N(6)-chloroacetyl-poly-L-lysine are dissolved in 1.5 ml of oxygen-free dimethylformamide at room temperature and under argon. 0.1 ml of oxygen-free water and 20.5 mg (0.054 mmol) of "N-acetylglucosaminothiol" are added. 15 mg (0.10 mmol) of 1,8-diazabicyclo[5.4.0]undec-7-ene(1,5-5) are then added to the clear solution. After having been stirred at room temperature for 2 h, the clear, colourless solution is added dropwise to 20 ml of diethyl ether/ethanol (1:1). The precipitate which has formed is filtered off and washed with ethanol. The crude product is dissolved in water and purified further by means of ultrafiltration (Amicon YM 3000 membrane). 23 mg of colourless product C3 are obtained after lyophilizing the residue. The content of carbohydrate is 100 mol % (determined by $^1$H NMR spectroscopy). The yield is 85%. n is approximately 250.

$^1$H-NMR (D$_2$O, 500 MHz), selected signals δ=4.45 (1H, d, 8.0 Hz, H$_1$); 4.00 (1H, s (br), C$\underline{H}$); 2.54 (2H, s (br), —NH—CO—C$\underline{H}_2$—CH$_2$—CH$_2$—S—); 2.29 (2H, s (br), —NH—CO—CH$_2$—CH$_2$—C$\underline{H}_2$—S—); 2.05–1.35 (6H, —CH—C$\underline{H}_2$—C$\underline{H}_2$—C$\underline{H}_2$—CH$_2$—NH—); 2.00 (30H, s, CO—CH$_3$); 1.81 (2H, m, —O—CH$_2$—C$\underline{H}_2$—CH$_2$—NH—CO—); 1.65 (2H, m, —NH—CO—CH$_2$—C$\underline{H}_2$—CH$_2$—S—). $\overline{M}_w$ (GPC/MALLS): 110,000 D b) Synthesis of Water-soluble Polylysine Derivatives Having a Defined Number of Pendent Saccharide Side Chains

EXAMPLE C4

Reaction of N(6)-Chloroacetyl-poly-L-lysine B1
With 50 mol % "N-Acetylglucosaminothiol" A1
and Then With Thioglycerol

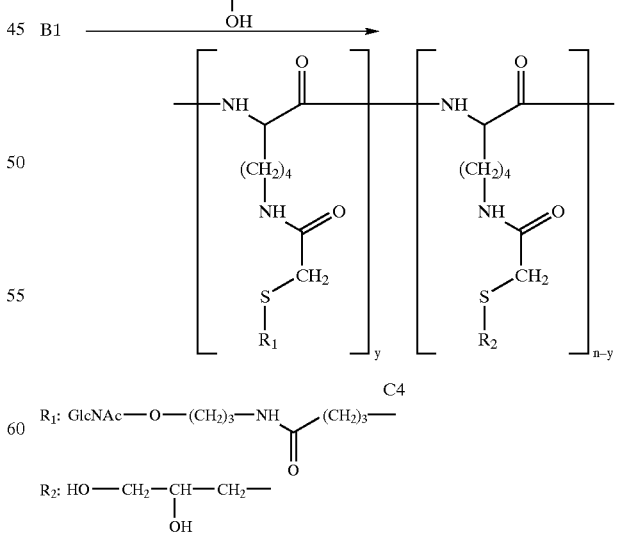

29 mg (0.14 mmol) of N(6)-chloroacetyl-poly-L-lysine are dissolved in 2 ml of oxygen-free dimethylformamide at room temperature and under argon. 27 mg (0.07 mmol) of "N-acetylglucosaminothiol" are added, after which 21 mg (0.14 mmol) of 1,8-diazabicyclo[5,4,0]undec-7-ene(1,5-5) are added to the clear solution. After stirring at room temperature for 4 h, 250 mg (2.32 mmol) of thioglycerol are added, followed by 100 μl of distilled triethylamine. After having been stirred at room temperature for 16 h, the clear, colourless solution is added dropwise to 20 ml of diethyl ether/ethanol (1:1). The precipitate which has formed is filtered off and washed with ethanol. The crude product is dissolved in water and purified further by means of ultrafiltration (Amicon YM 3000 membrane). 50 mg of colourless product are obtained after lyophilizing the residue. The content of carbohydrate is 50 mol % (determined by $^1$H NMR spectroscopy). The yield is 86%. n is approximately 250, y=n/2.

$^1$H-NMR (D$_2$O, 500 MHz), selected signals δ=4.45 (50/100H, d, 8.0 Hz, H$_1$); 4.00 (1H, s, (br), C$\underline{H}$); 2.67, 2.60 (je 50/100H, 2×dd, 13.5, 4.5/13.5, 7.5 Hz, —S—C$\underline{H}_2$—CH(OH)—CH$_2$—OH); 2.54 (2×50/100H, s (br), —NH—CO—C$\underline{H}_2$—CH$_2$—CH$_2$—S—); 2.29 (2×50/100H, t, 6.5 Hz, —NH—CO—CH$_2$—CH$_2$—C$\underline{H}_2$—S—); 2.05–1.35 (6H, —CH—C$\underline{H}_2$—C$\underline{H}_2$—C$\underline{H}_2$—CH$_2$—NH—); 2.00 (3×50/100H, s, CO—C$\underline{H}_3$); 1.81 (2×50/100H, m, —O—CH$_2$—C$\underline{H}_2$—CH$_2$—NH—CO—); 1.65 (2×50/100H, quint, 6.5 Hz; —NH—CO—CH$_2$—C$\underline{H}_2$—CH$_2$—S—). $\overline{M}_w$ (GPC/MALLS): 90,000 D.

EXAMPLE C5

Reaction of N(6)-Chloroacetyl-poly-D/L-lysine B3 With 50 mol % "N-Acetylglucosaminothiol" A1 and Then With Thioglycerol

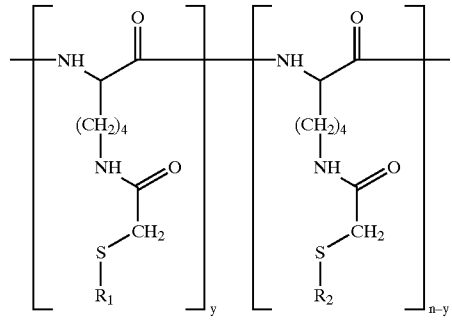

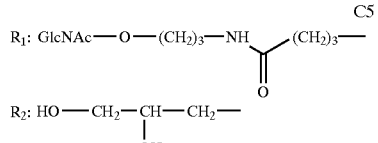

C5

10 mg (0.049 mmol) of N(6)-chloroacetyl-poly-D/L-lysine are dissolved in 1 ml of oxygen-free dimethylformamide at room temperature and under argon. 9.3 mg (0.025 mmol) of "N-acetylglucosaminothiol" are added, after which 7.5 mg (0.049 mmol) of 1,8-diazabicyclo[5.4.0]undec-7-ene(1,5-5) are added to the clear solution. After stirring at room temperature for 3 h, 100 mg (0.93 mmol) of thioglycerol are added, followed by 50 μl of distilled triethylamine. After having been stirred at room temperature for 16 h, the clear, colourless solution is added dropwise to 20 ml of diethyl ether/ethanol (1:1). The precipitate which has formed is filtered off and washed with ethanol. The crude product is dissolved in water and purified further by means of ultrafiltration (Amicon YM 3000 membrane). 19 mg of colourless product C5 are obtained after lyophilizing the residue. The content of carbohydrate is 50 mol % (determined by $^1$H NMR spectroscopy). The yield is 94%. n is approximately 250, y=n/2.

$^1$H-NMR (D$_2$O, 500 MHz), selected signals δ=4.45 (50/100H, d, 8.0 Hz, H$_1$); 4.21 (1H, s (br), C$\underline{H}$); 2.66, 2.60 (in each case 50/100H, 2×dd, 13.5, 4.5/13.5, 7.5 Hz, —S—C$\underline{H}_2$—CH(OH)—CH$_2$—OH); 2.54 (2×50/100H, t, 6.5 Hz, —NH—CO—C$\underline{H}_2$—CH$_2$—CH$_2$—S—); 2.29 (2×50/100H, t, 6.5 Hz, —NH—CO—CH$_2$—CH$_2$—C$\underline{H}_2$—S—); 1.99 (3×50/100H, s, CO—C$\underline{H}_3$); 1.81 (2×50/100H, quint, 6.5 Hz, —O—CH$_2$—C$\underline{H}_2$—CH$_2$—NH—CO—); 1.65 (2×50/100H, quint, 6.5 Hz; —NH—CO—CH$_2$—C$\underline{H}_2$—CH$_2$—S—); 1.50 (2H, S, —CH—CH$_2$—CH$_2$—C$\underline{H}_2$—CH$_2$—NH—); 1.34 (2H, —CH—CH$_2$—C$\underline{H}_2$—CH$_2$—CH$_2$—NH—).

EXAMPLE C6

Reaction of N(6)-Chloroacetyl-poly-L-lysine B1 With 20 mol % of "Sialyl-lewis x thiol" A2 and Then With Thioglycerol

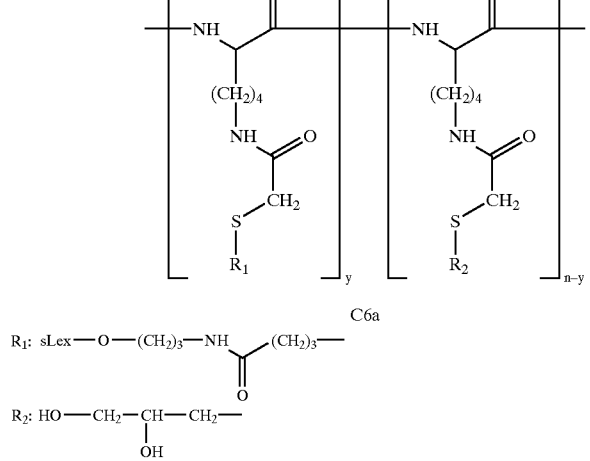

C6a

R$_1$: sLex—O—(CH$_2$)$_3$—NH—C(=O)—(CH$_2$)$_3$—

R$_2$: HO—CH$_2$—CH(OH)—CH$_2$—

7.0 mg (0.035 mmol) of N(6)-chloroacetyl-poly-L-lysine are dissolved in 1.5 ml of oxygen-free dimethylformamide at room temperature and under argon. An oxygen-free solution of 7.0 mg (0.007 mmol) of "sialyl-Lewis x thiol" in 0.5 ml of dimethylformamide/water (4:1) is added. 5.3 mg (0.035 mmol) of 1,8-diazabicyclo[5.4.0]undec-7-ene(1,5-5) are then added. After stirring at room temperature for 6 h, 50 mg (0.46 mmol) of thioglycerol are added, followed by 50 μl of distilled triethylamine. After having been stirred at room temperature for 16 h, the clear, colourless solution is added dropwise to 20 ml of diethyl ether/ethanol (1:1). The precipitate which has formed is filtered off and washed with ethanol. The crude product is dissolved in water, and this solution is adjusted to pH 11 with sodium hydroxide solution and the crude product is purified further by means of ultrafiltration (Amicon YM 3000 membrane) (five times from 12 down to 2 ml, with distilled water being used to make up the volume in each case). 13 mg of colourless product C6a are obtained after lyophilizing the residue. The content of carbohydrate is 20 mol % (determined by $^1$H NMR spectroscopy). The yield is 82%. n is approximately 250, and y is approximately 50.

$^1$H-NMR (D$_2$O, 500 MHz), selected signals δ=5.05 (20/100H, d, 4.0 Hz, Fuc-H$_1$); 4.46 (2×20/100H, d, 8.0 Hz, Gal-H$_1$ and GlcNAc-H$_1$); 4.03 (20/100H, d (br), 10.0 Hz); 4.00 (1H, s (br), lysine-Hα); (3.96 (1H, d (br), 12.0 Hz); 2.72 (20/100H, dd, 12.0/4.0 Hz, Sia-H$_{3a}$); 2.72, 2.60 (in each case 80/100H, 2×dd, 13.5, 4.5/13.5, 7.5 Hz, —S—C$\underline{H}_2$—CH(OH)—CH$_2$—OH); 2.54 (2×20/100H, t, 7.0 Hz, —NH—CO—CH$_2$—CH$_2$—C$\underline{H}_2$—S—); 2.29 (2×20/100H, t, —NH—CO—C$\underline{H}_2$—CH$_2$—CH$_2$—SH—); 1.98 (6×20/100H, s, 2×CO—C$\underline{H}_3$); 1.83 (2×20/100H, quint, 7.5 Hz, —NH—CO—CH$_2$—C$\underline{H}_2$—CH$_2$—S—); 1.75 (20/100H, t, 12.0 Hz, Sia-H$_{3b}$); 1.70 (2×20/100H, quint, 6.0 Hz, —O—CH$_2$—C$\underline{H}_2$—NH—).

98 and 95%. n is approximately 250, and y is given in the following table.

$^1$H NMR (D$_2$O, 500 MHz) of polymer C7b containing 30 mol % sialyl-Lewis x; selected signals δ=5.05 (30/100H, d, 4.0 Hz, Fuc-H$_1$); 4.46 (2×30/100H, d, 8.0 Hz, Gal-H$_1$ and GlcNAc-H$_1$); 4.21 (1H, s (br), lysine-Hα); 4.03 (30/100H, d (br), 10.0 Hz); (3.96 (30/100H, d (br), 12.0 Hz); 2.72 (30/100H, dd, 12.0/4.0 Hz, Sia-H$_{3a}$); 2.72, 2.60 (in each case 70/100H, 2×dd, 13.5, 4.5/13.5, 7.5 Hz, —S—C$\underline{H}_2$—CH(OH)—CH$_2$—OH); 2.54 (2×30/100H, t, 7.0 Hz, —NH—CO—CH$_2$—CH$_2$—C$\underline{H}_2$—S—); 2.29 (2×30/100H, t, —NH—CO—C$\underline{H}_2$—CH$_2$—CH$_2$—S—); 1.98 (6×30/100H, s, 2×CO—C$\underline{H}_3$); 1.83 (2×30/100H, quint, 7.5 Hz, —NH—CO—CH$_2$—C$\underline{H}_2$—CH$_2$—S—); 1.75 (30/100H, t, 12.0 Hz, Sia-H$_{3b}$); 1.70 (2×30/100H, quint, 6.0 Hz, —O—CH$_2$—C$\underline{H}_2$—CH$_2$—NH—).

| Product | Content of sLex in mol % | y | Content of thioglycerol in mol % |
|---|---|---|---|
| C6a | 20 | 50 | 80 |
| C6b | 5 | 13 | 95 |
| C6c | 10 | 25 | 90 |
| C6d | 15 | 38 | 85 |
| C6e | 30 | 75 | 70 |

Analogous reactions with 5, 10, 15 and 30 mol % "sialyl-Lewis x thiol" afford polymers C6b, C6c, C6d and C6e having sialyl-Lewis x contents of 5, 10, 15 and 30 mol % (ascertained by $^1$H NMR spectrocopy) in yields of 77, 98, 65 and 84%.

EXAMPLE C7

Reaction of N(6)-Chloroacetyl-poly-D/L-lysine B3 With "Sialyl-Lewis x Thiol" A2 and Then With Thioglycerol

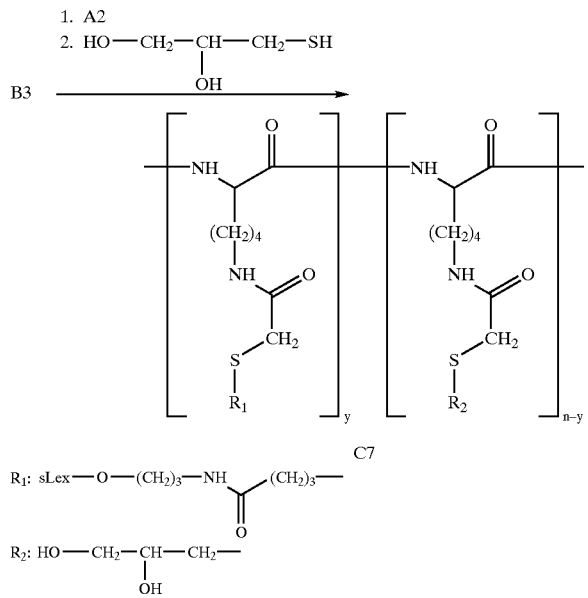

Analogous reactions of N(6)-chloroacetyl-poly-D/L-lysine with 10 or 30 mol % "sialyl-Lewis x thiol" afford polymers C7a and C7b having sialyl-Lewis x contents of 10 and 30 mol % (ascertained by $^1$H NMR spectroscopy) in yields of

| Product | Content of sLex in mol % | y | Content of thioglycerol in mol % |
|---|---|---|---|
| C7a | 10 | 25 | 60 |
| C7b | 30 | 75 | 70 | c) Synthesis of Biotinylated Polylysine Derivatives Having Pendent Saccharide Side Chains

EXAMPLE C8

Reaction of N(6)-Chloroacetyl-poly-L-lysine B1 With 20 mol % "Sugar Thiol" A2. 5 mol % "Biotinthiol" A3 and Then With Thioglycerol

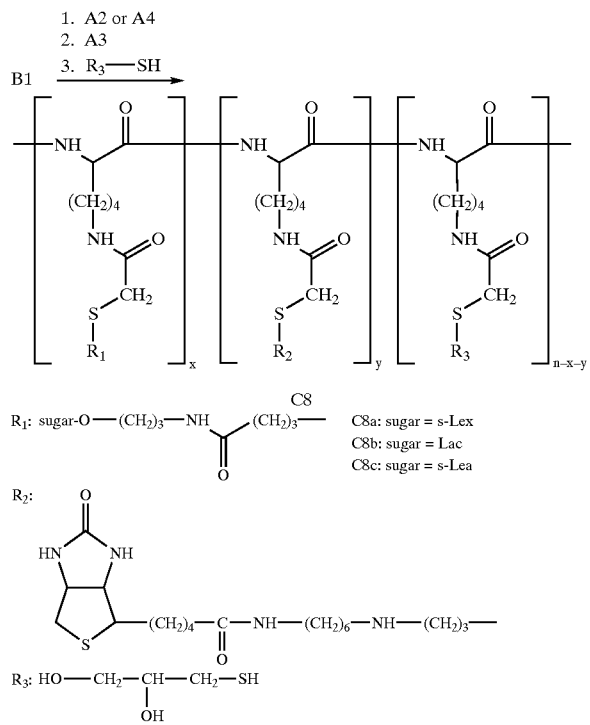

10.0 mg (0.049 mmol) of N(6)-chloroacetyl-poly-L-lysine, 10.6 mg (0.010 mmol) of "sialyl-Lewis x thiol" A2 and 1.1 mg (0.0025 mmol) of "biotinthiol" are dissolved in 2 ml of oxygen-free dimethylformamide at room temperature and under argon. 0.1 ml of oxygen-free water and 7.5 mg (0.049 mmol) of 1,8-diazabicyclo[5.4.0]undec-7-ene(1,5-5) are added to the clear, colourless solution. After stirring at room temperature for 3 h, 50 mg (0.46 mmol) of thioglycerol are added, followed by 50 μl of distilled triethylamine. After having been stirred at room temperature for 16 h, the clear, colourless solution is added dropwise to 20 ml of diethyl ether/ethanol (1:1). The precipitate which has formed is filtered off and washed with ethanol. The crude product is dissolved in water and this solution is adjusted to pH 11 with sodium hydroxide solution and the crude product is further purified by ultrafiltration (Amicon YM 3000 membrane) (five times from 12 down to 2 ml, with the volume being made up with distilled water in each case). 22 mg of colourless product C8a are obtained after lyophilizing the residue. The content of carbohydrate is 20 mol % and the content of biotin is 5 mol % (determined by $^1$H NMR spectroscopy). The yield is 95%. n is approximately 250, x is approximately 50 and y is approximately 13.

$^1$H-NMR (D$_2$O, 500 MHz), selected signals δ=5.05 (20/100H, d, 4.0 Hz, Fuc-H$_1$); 4.55 (5/100H, m, biotin-H); 4.46 (2×20/100H, d, 8.0 Hz, Gal-H$_1$ and GlcNAc-H$_1$); 4.37 (5/100 H, m, biotin-H); 4.03 (20/100H, d (br), 10.0 Hz); 4.00 (1H, s (br), lysine-Ha); 3.96 (20/100H, d (br), 12.0 Hz); 2.93 (5/100 H, m, biotin-H); 2.72 (5/100 H, m, biotin-H), 2.72 (20/100H, dd, 12.0/4.0 Hz, Sia-H$_{3a}$); 2.72, 2.60 (in each case 75/100H, 2×dd, 13.5, 4.5/13.5, 7.5 Hz, —S—CH$_2$—CH(OH)—CH$_2$—OH); 2.54 (2×25/100H, t, 7.0 Hz, —NH—CO—CH$_2$—CH$_2$—CH$_2$—S—); 2.29 (2×25/100H, t, —NH—CO—CH$_2$—CH$_2$—CH$_2$—S—); 1.98 (6×20/100H, s, 2×CO—CH$_3$); 1.83 (2×25/100H, quint, 7.5 Hz, —NH—CO—CH$_2$—CH$_2$—CH$_2$—S—); 1.75 (20/100H, t, 12.0 Hz, Sia-H$_{3b}$); 1.70 (2×20/100H, quint,6.0 Hz, —O—CH$_2$—CH$_2$—CH$_2$—NH—).

If the 's-Lex thiol' A2 is replaced by a corresponding 'lactose thiol' A4, but the conduct of the reaction is otherwise unchanged, an analogous polymer C8b is obtained in 95% yield which contains 20 mol % of the lactose derivative instead of 20 mol % of s-Lex.

$^1$H-NMR (D$_2$O, 500 MHz), selected signals δ=4.55 (5/100 H, m, biotin-H); 4.45 and 4.44 (2×20/100H, d, 8.0 Hz, Gal-H$_1$ and Glc-H$_1$); 4.37 (5/100 H, m, biotin-H); 4.06–3.85 (7×20/100H, m, lactose derivative); 4.00 (1H, s (br), lysine-Ha); 2.93 (5/100 H, m, biotin-H); 2.72 (5/100 H, m, biotin-H); 2.72, 2.60 (in each case 75/100H, 2×dd, 13.5, 4.5/13.5, 7.5 Hz, —S—CH$_2$—CH(OH)—CH$_2$—OH); 2.54 (2×25/100H, t, 7.0 Hz, —NH—CO—CH$_2$—CH$_2$—CH$_2$—S—); 2.29 (2×25/100H, t, —NH—CO—CH$_2$—CH$_2$—CH$_2$—S—); 1.83 (2×25/100H, quint, 7.5 Hz, —NH—CO—CH$_2$—CH$_2$—CH$_2$—S—); 1.70 (2×20/100H, quint, 6.0 Hz, —O—CH$_2$—CH$_2$—CH$_2$—NH—).

If the 's-Lex thiol' A2 is replaced by a corresponding 's-Lea thiol' A5, but the conduct of the reaction is otherwise unchanged, an analogous polymer C8c is obtained in 93% yield which contains 20 mol % of s-Lea instead of 20 mol % of s-Lex.

1H-NMR (D2O, 500 MHz), selected signals δ=4.97 (20/100 H, d, 4.0 Hz, Fuc-H1); 4.84 (20/100H, q (br), 7.0 Hz, Fuc-H5); 4.57 (5/100 H, m, biotin-H); 4.49,4.48 (2×20/100H, d, 8.0 Hz, Gal-H1 and GlcNAc-H1); 4.39 (5/100 H, m, biotin-H); 4.05–3.90 (4×20/100H, s-Lea +1H, s (br), lysine-Ha); 3.96 (20/100H, d (br),12.0 Hz); 2.93 (5/100 H, m, biotin-H); 2.72 (5/100 H, m, biotin-H), 2.72 (20/100H, dd, 12.0/4.0 Hz, Sia-H$_{3a}$); 2.72, 2.60 (in each case 75/100H, 2×dd, 13.5, 4.5/13.5, 7.5 Hz, —S—CH2—CH(OH)—CH2—OH); 2.54 (2×25/100H, t, 7.0 Hz, —NH—CO—CH2—CH2—CH2—S—); 2.29 (2×25/100H, t, —NH—CO—CH2—CH2—CH2—S—); 1.98 (6×20/100H, s, 2×CO—CH3); 1.83 (2×25/100H, quint, 7.5 Hz, —NH—CO—CH2—CH2—CH2—S—); 1.75(20/100H, t, 12.0 Hz, Sia-H$_{3b}$); 1.70 (2×20/100H, quint, 6.0 Hz, —O—CH2—CH2—CH2—NH—).

d) Synthesis of Polylysine Derivatives Having Pendent Saccharide, Acid and Thioglycerol Side Chains

EXAMPLE C9

Reaction of N(6)-Chloroacetyl-poly-L-lysine B1 With 20 mol % "Sialyl-Lewis x Thiol" A2. 25 mol % Sodium 2-Mercaptoacetate and Then With Thioglycerol

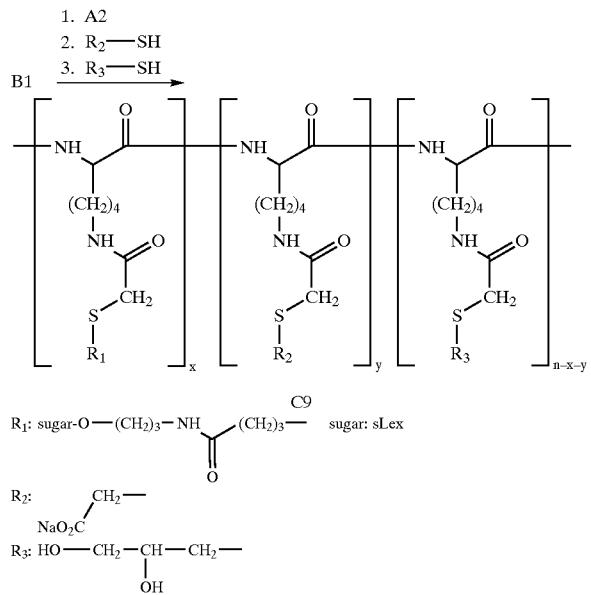

6.6 mg (0.0324 mmol) of N(6)-chloroacetyl-poly-L-lysine, 6.5 mg (0.0065 mmol) of "sialyl-Lewis x thiol" and 0.92 mg (0.0081 mmol) of sodium 2-mercaptoacetate are dissolved in 1 ml of oxygen-free dimethylformamide at room temperature and under argon. 0.05 ml of oxygen-free water are added to the slightly turbid solution. 4.9 mg (0.0324 mmol) of 1,8-diazabicyclo[5.4.0]undec-7-ene(1,5-5) are added to the solution which is now clear. After stirring at room temperature for 3 h, 17.5 mg (0.162 mmol) of thioglycerol are added, followed by 25 μl of distilled triethylamine. After having been stirred at room temperature for 16 h, the clear, colourless solution is added dropwise to 15 ml of diethyl ether/ethanol (2:1). The precipitate which has formed is filtered off and washed with ether. The crude product is dissolved in water and this solution is adjusted to pH 11 with sodium hydroxide solution, and the crude product is further purified by means of ultrafiltration (Amicon YM 3000 membrane) (five times from 12 down to 2 ml, with the volume being made up with distilled water on each occasion). 15 mg of colourless product C9 are obtained after lyophilizing the residue. The content of carbohydrate is 20 mol %, and the content of mercaptoacetic acid is 25 mol % (determined by $^1$ H NMR spectroscopy). The yield is quantitative. n is approximately 250, x is approximately 50 and y is approximately 63.

$^1$H-NMR (D$_2$O, 500 MHz), selected signals δ=5.05 (20/100H, d, 4.0 Hz, Fuc-H$_1$); 4.46 (2×20/100H, d, 8.0 Hz, Gal-H$_1$ and GlcNAc-H$_1$); 4.03 (20/100H, d (br), 10.0 Hz);

4.00 (1H, s (br), lysine-Hα); 3.96 (1H, d (br), 12.0 Hz); 3.22 (2×25/100H, s, —S—C$\underline{H}_2$—COONa); 2.72 (20/100H, dd, 12.0/4.0 Hz, Sia-H$_{3a}$); 2.72, 2.60 (in each case 55/100H, 2×dd, 13.5, 4.5/13.5, 7.5 Hz, —S—C$\underline{H}_2$—CH(OH)—CH$_2$—OH); 2.54 (2×20/100H, t, 7.0 Hz, —NH—CO—CH$_2$—CH$_2$—C$\underline{H}_2$—S—); 2.29 (2×20/100H, t, —NH—CO—C$\underline{H}_2$—CH$_2$—CH$_2$—S—); 1.98 (6×20/100H, s, 2 ×CO—CH$_3$); 1.83 (2×20/100H, quint, 7.5 Hz, —NH—CO—CH$_2$—C$\underline{H}_2$—CH$_2$—S—); 1.75 (20/100H, t, 12.0 Hz, Sia-H$_{3b}$); 1.70 (2×20/100H, quint, 6.0 Hz, —O—CH$_2$—C$\underline{H}_2$—CH$_2$—NH—).

EXAMPLE C10

Reaction of N(6)-Chloroacetyl-poly-L-lysine B1 With 20 mol % "Sialyl-Lewis x Thiol" A2. 25 mol % Sodium 2-Mercapto-ethanesulfonate and Then With Thioglycerol

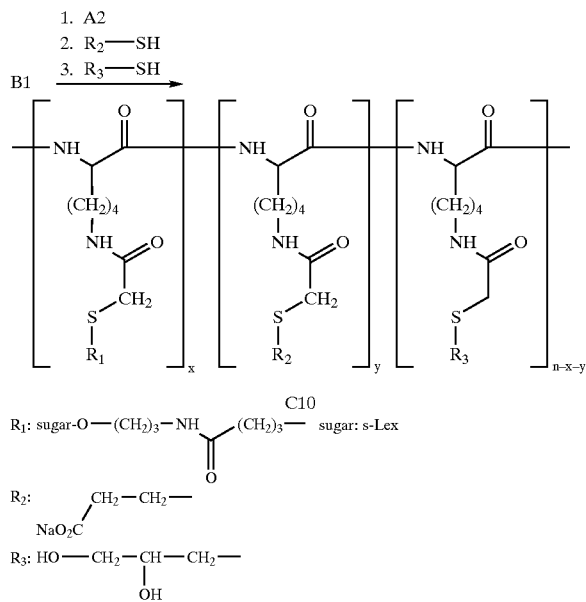

C10

6.6 mg (0.0324 mmol) of N(6)-chlorbacetyl-poly-L-lysine, 6.5 mg (0.0065 mmol) of "sialyl-Lewis x thiol" and 1.33 mg (0.0081 mmol) of sodium 2-mercaptoethanesulfonate are dissolved in 1 ml of oxygen-free dimethyiformamide at room temperature and under argon. 0.05 ml of oxygen-free water are added to the slightly turbid solution. 4.9 mg (0.0324 mmol) of 1,8-diazabicyclo[5.4.0]undec-7-ene(1,5-5) are added to the solution, which is now clear. After stirring at room temperature for 3 h. 17.5 mg (0.162 mmol) of thioglycerol are added, followed by 25 μl of distilled triethylamine. After having been stirred at room temperature for 16 h, the clear, colourless solution is added dropwise to 15 ml of diethyl ether/ethanol (2:1). The precipitate which has formed is filtered off and washed with ether. The crude product is dissolved in water and the pH of this solution is adjusted to 11 with sodium hydroxide solution, and the crude product is further purified by means of ultrafiltration (Amicon YM 3000 membrane) (five times from 12 down to 2 ml, with the volume being made up with distilled water on each occasion). 15 mg of colourless product C10 are obtained after lyophilizing the residue. The content of carbohydrate is 20 mol %, and the content of mercaptoethanesulfonate is 25 mol % (determined by $^1$H NMR spectroscopy). The yield is quantitative. n is approximately 250, x is approximately 50 and y is approximately 63.

$^1$H-NMR (D$_2$O, 500 MHz), selected signals δ=5.05 (20/100H, d, 4.0 Hz, Fuc-H$_1$); 4.46 (2×20/100H, d, 8.0 Hz, Gal-H$_1$ and GlcNAc-H$_1$); 4.03 (20/100H, d (br), 10.0 Hz); 4.00 (1H, s (br), lysine-Hα); 3.96 (1H, d (br), 12.0 Hz); 3.12 (2×25/100H, t(br), 7.5 Hz, , —S—C$\underline{H}_2$—CH$_2$—SO$_3$Na); 2.87 (2×25/100H, t(br), 7.5 Hz, —S—CH$_2$—C$\underline{H}_2$—SO$_3$Na); 2.72 (20/100H, dd, 12.0/4.0 Hz, Sia-H$_{3a}$); 2.72, 2.60 (in each case 55/100H, 2×dd, 13.5, 4.5/13.5, 7.5 Hz, —S—C$\underline{H}_2$—CH(OH)—CH$_2$—OH); 2.54 (2×20/100H, t, 7.0 Hz, —NH—CO—CH$_2$—CH$_2$—C$\underline{H}_2$—S—); 2.29 (2×20/100H, t, —NH—CO—C$\underline{H}_2$—CH$_2$—CH$_2$—S—); 1.98 (6×20/100H, s, 2×CO—CH$_3$); 1.83 (2×20/100H, quint, 7.5 Hz, —NH—CO—CH$_2$—C$\underline{H}_2$—CH$_2$—S—); 1.75 (20/100H, t, 12.0 Hz, Sia-H$_{3b}$); 1.70 (2×20/100H, quint, 6.0 Hz, —O—CH$_2$—C$\underline{H}_2$—CH$_2$—NH—).

e) Synthesis of Polylysine Derivatives Having Pendent Saccharide, Acid and Biotin Side Chains

EXAMPLE C11

Reaction of N(6)-Chloroacetyl-poly-L-lysine B1 With 20 mol % "Sialyl-Lewis x Thiol" A2. 5 mol % "Biotin Thiol" A3 and Then With 3-Mercaptopropionic Acid

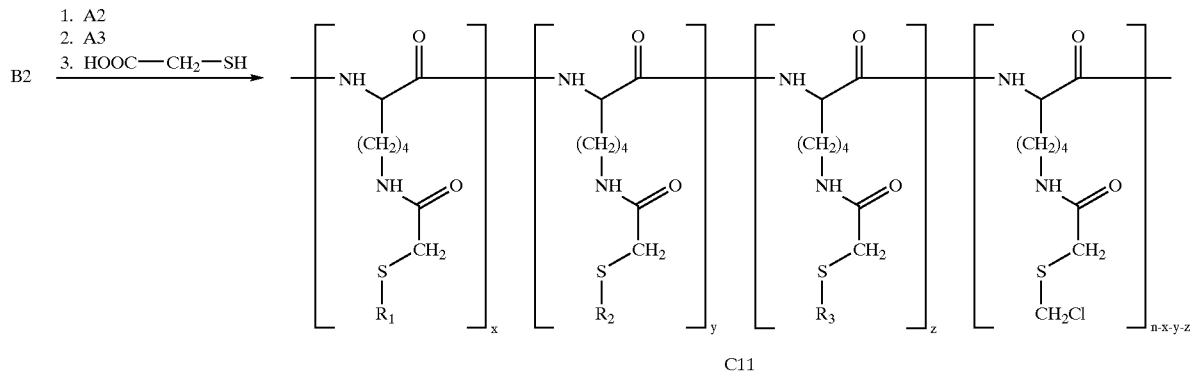

C11

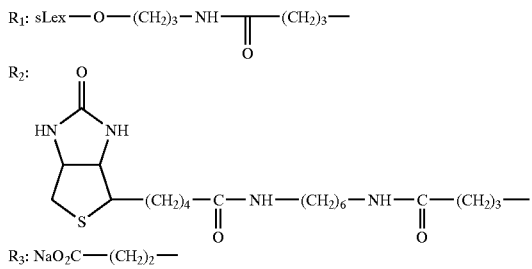

R₁: sLex—O—(CH₂)₃—NH—C(=O)—(CH₂)₃—

R₂: biotin—(CH₂)₄—C(=O)—NH—(CH₂)₆—NH—C(=O)—(CH₂)₃—

R₃: NaO₂C—(CH₂)₂—

25.0 mg (0.122 mmol) of N(6)-chloroacetyl-poly-L-lysine, 26.4 mg (0.024 mmol) of "sialyl-Lewis x thiol" A2 and 2.70 mg (0.0061 mmol) of "biotin thiol" A3 are dissolved, in succession, in 2.5 ml of oxygen-free dimethylformamide at room temperature and under argon. 18.5 mg (0.122 mmol) of 1,8-diazabicyclo[5.4.0]undec-7-ene(1,5-5) are added to the clear solution. After stirring at room temperature for 1 h, 38.8 mg (0.366 mmol) of 3-mercaptopropionic acid and 100 μl of distilled triethylamine are added, followed by 0.5 ml of water. After having been stirred at room temperature for 16 h, the clear, colourless solution is added dropwise to 15 ml of diethyl ether/ethanol (2:1). The precipitate which is formed is filtered off and washed with ether. The crude product is dissolved in water and this solution is adjusted to pH 11 with sodium hydroxide solution, and the crude product is further purified by means of ultrafiltration (Amicon YM 3000 membrane) (five times from 12 down to 2 ml, with the volume being made up with distilled water on each occasion). 60 mg of colourless product C11 are obtained after lyophilizing the residue. The content of carbohydrate is 20 mol %, the content of biotin is 5 mol % and the content of 3-mercaptopropionic acid is 60 mol %. The content of remaining chloroacetamide is 15 mol % (determined by ¹H NMR spectroscopy). The yield is quantitative. n is approximately 250, x is approximately 50, y is approximately 13 and z is approximately 150.

¹H-NMR (D₂O, 500 MHz), selected signals δ=5.07 (20/100H, d, 4.0 Hz, Fuc-H₁); 4.57 (5/100H, m, biotin); 4.48 (2×20/100H, d, 8.0 Hz, Gal-H₁ and GlcNAc-H₁); 4.38 (5/100H, m, biotin); 4.22 (1H, s (br), lysine-Hα); 4.07 (2×15/100H, s, —CH₂—Cl); 2.95 (5/100H, m, biotin); 2.85 (5/100H, m, biotin); 2.73 (2×60/100H+20/100H, m, —S—CH₂—CH₂—CO₂Na, Sia-H₃ₐ); 2.54 (2×25/100H, t, 7.0 Hz, —NH—CO—CH₂—CH₂—CH₂—S—); 2.43 (2×60/100H, t, 6.5 Hz, —S—CH₂—CH₂—CO₂Na); 2.29 (2×25/100H, t, —NH—CO—CH₂—CH₂—CH₂—S—); 2.21 (2×5/100H, t, 6.5 Hz, biotin); 1.98 (6×20/100H, s, 2×CO—CH₃); 1.12 (3×20/100H, d, 6.5 Hz, Fuc-H₆).

EXAMPLE C12

Reaction of N(6)-Chloroacetyl-poly-L-lysine B1 With 20 mol % "Sialyl-Lewis x Thiol" A2. 5 mol % "Biotin Thiol" A3 and Then With Sodium 2-Mercaptoethanesulfonate

B1 →(1. A2; 2. A3; 3. R₃—SH)→

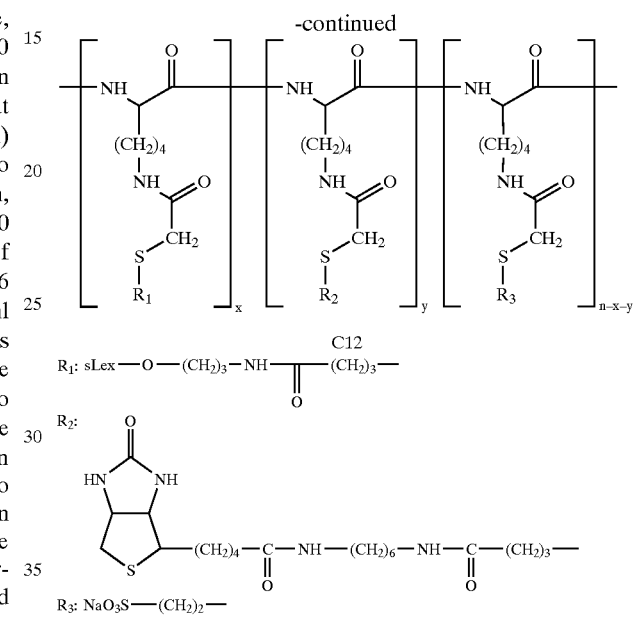

C12
R₁: sLex—O—(CH₂)₃—NH—C(=O)—(CH₂)₃—

R₂: biotin—(CH₂)₄—C(=O)—NH—(CH₂)₆—NH—C(=O)—(CH₂)₃—

R₃: NaO₃S—(CH₂)₂—

25.0 mg (0.122 mmol) of N(6)-chloroacetyl-poly-L-lysine, 26.4 mg (0.024 mmol) of "sialyl-Lewis x thiol" A2 and 2.70 mg (0.0061 mmol) of "biotin thiol" A3 are dissolved, in succession, in 2.5 ml of oxygen-free dimethylformamide at room temperature and under argon. 18.5 mg (0.122 mmol) of 1,8-diazabicyclo[5.4.0]undec-7-ene(1,5-5) are added to the clear solution. After stirring at room temperature for 1 h, 60 mg (0.366 mmol) of sodium 2-mercaptoethanesulfonate and 100 μl of distilled triethylamine are added, followed by 0.5 ml of water. After having been stirred at room temperature for 16 h, the clear, colourless solution is added dropwise to 15 ml of diethyl ether/ethanol (2:1). The precipitate which has formed is filtered off and washed with ether. The crude product is dissolved in water and this solution is adjusted to pH 11 with sodium hydroxide solution, and the crude product is further purified by means of ultrafiltration (Amicon YM 3000 membrane) (five times from 12 down to 2 ml, with the volume being made up with distilled water on each occasion). 60 mg of colourless product C12 are obtained after lyophilizing the residue. The content of carbohydrate is 20 mol %, the content of biotin is 5 mol % and the content of 2-mercaptoethanesulfonate is 75 mol %. (determined by ¹H NMR spectroscopy). The yield is quantitative. n is approximately 250, x is approximately 50 and y is approximately 13.

$^1$H-NMR (D$_2$O, 500 MHz), selected signals δ=5.08 (20/100H, d, 4.0 Hz, Fuc-H$_1$); 4.57 (5/100H, m, biotin); 4.49 (2×20/100H, d, 8.0 Hz, Gal-H$_1$ and GlcNAc-H$_1$); 4.38 (5/100H, m, biotin); 4.26 (1H, s (br), lysine-Hα); 2.95 (5/100H, m, biotin); 2.87 (2×75/100H+5/100H, m, —S—C$\underline{H}_2$—CH$_2$—SO$_3$Na, biotin); 2.73 (20/100H, m, Sia-H$_{3a}$); 2.55 (2×25/100H, t, 7.0 Hz, —NH—CO—CH$_2$—CH$_2$—C$\underline{H}_2$—S—); 2.30 (2×25/100H, t, 7.0 Hz, —NH—CO—C$\underline{H}_2$—CH$_2$—CH$_2$—S—); 2.21 (2×5/100H, t, 6.5 Hz, biotin); 1.98 (6×20/100H, s, 2×CO—C$\underline{H}_3$); 1.12 (3×20/100H, d, 6.5 Hz, Fuc-H$_6$).

f) Synthesis of Polylysine Derivatives Having Pendent Saccharide, Acid, Biotin and Thioglycerol Side Chains

EXAMPLE C13

Reaction of N(6)-Chloroacetyl-poly-L-lysine B1 With 20 mol % "Sialyl-Lewis x Thiol" A2, 5 mol % "Biotin Thiol" A3, 3-Mercaptopropionic Acid and Then Thioalycerol

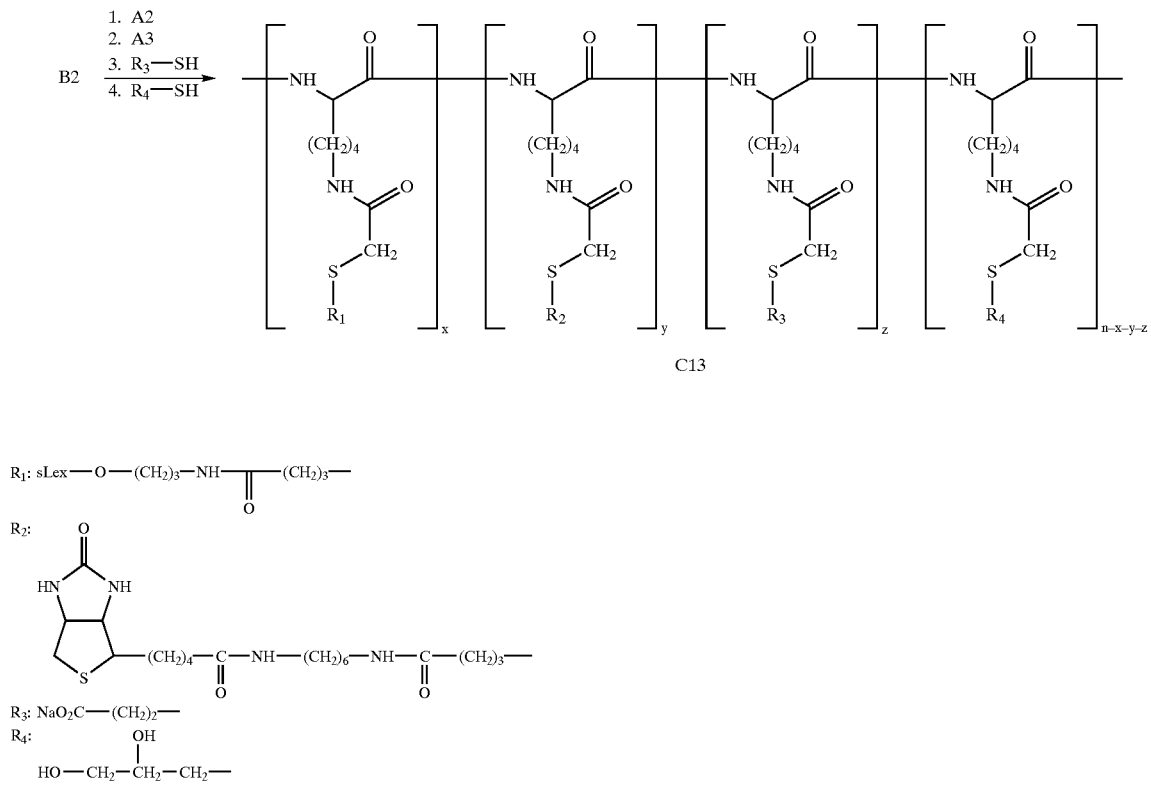

C13

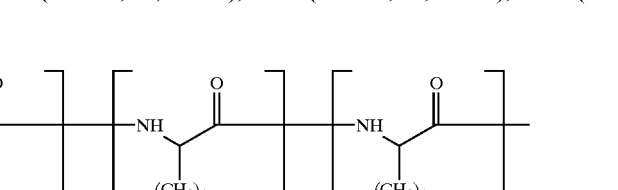

25.0 mg (0.122 mmol) of N(6)-chloroacetyl-poly-L-lysine, 26.4 mg (0.024 mmol) of "sialyl-Lewis x thiol" A2, 2.70 mg (0.0061 mmol) of "biotin thiol" A3 and 3.2 mg (0.0305 mmol) 3-mercaptopropionic acid are dissolved, in succession, in 3.0 ml of oxygen-free dimethylformamide at room temperature and under argon. 27.8 mg (0.183 mmol) of 1,8-diazabicyclo[5.4.0]undec-7-ene(1,5-5) are added to the clear solution. After stirring at room temperature for 1 h, 39.5 mg (0.366 mmol) of thioglycerol and 100 μl of distilled triethylamine are added, followed by 0.5 ml of water. After having been stirred at room temperature for 1 h, the clear, colourless solution is added dropwise to 15 ml of diethyl ether/ethanol (2:1). The precipitate which has formed is filtered off and washed with ether. The crude product is dissolved in water and this solution is adjusted to pH 11 with sodium hydroxide solution, and the crude product is further purified by means of ultrafiltration (Amicon YM 3000 membrane) (five times from 12 down to 2 ml, with the volume being made up with distilled water on each occasion). 60 mg of colourless product C13 are obtained after lyophilizing the residue. The content of carbohydrate is 20 mol %, the content of biotin is 5 mol %, and the content of 3-mercaptopropionic acid is 25 mol % (determined by $^1$H NMR spectroscopy). The yield is quantitative. n is approximately 250, x is approximately 50, y is approximately 13 and z is approximately 63.

$^1$H-NMR (D$_2$O, 500 MHz), selected signals δ=5.08 (20/100H, d, 4.0 Hz, Fuc-H$_1$); 4.57 (5/100H, m, biotin); 4.49 (2×20/100H, d, 8.0 Hz, Gal-H$_1$ and GlcNAc-H$_1$); 4.38 (5/100H, m, biotin); 2.93 (5/100H, m, biotin); 2.75 (50/100H +2×25/100H+20/100H+5/100H, m, —S—C$\underline{H}_a$H$_b$—CH(OH)—CH$_2$—OH, —S—C$\underline{H}_2$—CH$_2$—CO$_2$Na, Sia-H$_{3a}$, biotin); 2.60 (50/100H, dd, 13.5, 7.5 Hz, —S—CH$_a$H$_b$—CH(OH)—CH$_2$—OH); 2.55 (2×25/100H, t, 7.0 Hz, —NH—CO—CH$_2$—CH$_2$—C$\underline{H}_2$—S—); 2.43 (2×25/100H, t, 6.5 Hz, —S—CH$_2$—C$\underline{H}_2$—CO$_2$Na); 2.30 (2×25/100H, t, 7.0 Hz, —NH—CO—C$\underline{H}_2$—CH$_2$—CH$_2$—S—); 2.21 (2×5/100H, t, 6.5 Hz, biotin); 1.98 (6×20/100H, s, 2×CO—C$\underline{H}_3$); 1.13 (3×20/100H, d, 6.5 Hz, Fuc-H$_6$).

EXAMPLE C14

Reaction of N(6)-Chloroacetyl-poly-L-lysine B1 With 20 mol % "Sialyl-Lewis x Thiol" A2. 5 mol % "Biotin Thiol" A3. 2-Mercaptoethane-sulfonate and Then Thioglycerol

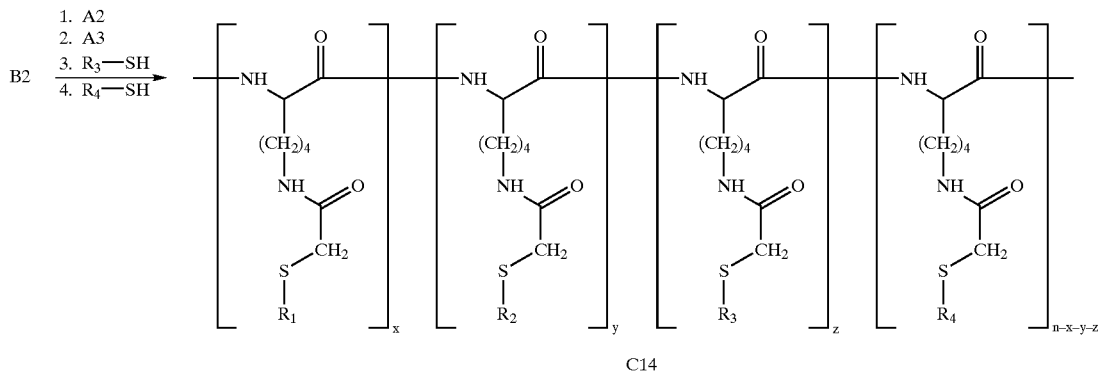

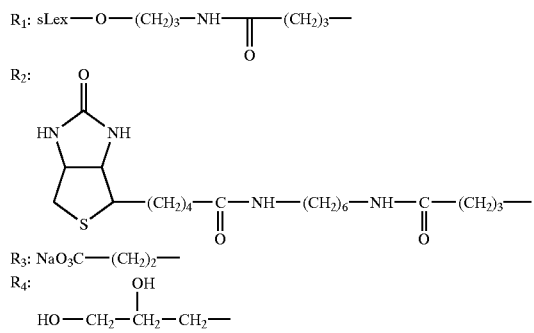

25.0 mg (0.122 mmol) of N(6)-chloroacetyl-poly-L-lysine, 26.4 mg (0.024 mmol) of "sialyl-Lewis x thiol" A2, 2.70 mg (0.0061 mmol) of "biotin thiol" A3 and 5.0 mg (0.0305 mmol) of 2-mercaptoethanesulfonate are dissolved, in succession, in 3.0 ml of oxygen-free dimethylformamide at room temperature and under argon. 27.8 mg (0.183 mmol) of 1,8-diazabicyclo[5.4.0]undec-7-ene(1,5-5) are added to the clear solution. After stirring at room temperature for 1 h, 39.5 mg (0.366 mmol) of thioglycerol and 100 µl of distilled triethylamine are added, followed by 0.5 ml of water. After having been stirred at room temperature for 2 h, the clear, colourless solution is added dropwise to 15 ml of diethyl ether/ethanol (2:1). The precipitate which has formed is filtered off and washed with ether. The crude product is dissolved in water and this solution is adjusted to pH 11 with sodium hydroxide solution, and the crude product is further purified by means of ultrafiltration (Amicon YM 3000 membrane) (five times from 12 down to 2 ml, with the volume being made up with distilled water on each occasion). 60 mg of colourless product C14 are obtained after lyophilizing the residue. The content of carbohydrate is 20 mol %, the content of biotin is 5 mol % and the content of 2-mercaptoethanesulfonate is 25 mol %. (determined by $^1$H NMR spectroscopy). The yield is quantitative. n is approximately 250, x is approximately 50, y is approximately 13 and z is approximately 63.

$^1$H-NMR (D$_2$O, 500 MHz), selected signals δ=5.08 (20/100H, d, 4.0 Hz, Fuc-H$_1$); 4.57 (5/100H, m, biotin); 4.49 (2×20/100H, d, 8.0 Hz, Gal-H$_1$ and GlcNAc-H$_1$); 4.38 (5/100H, m, biotin); 2.93 (5/100H, m, biotin); 2.90 (2×25/100H+5/100H, m, —S—C$\underline{H}_2$—CH$_2$—SO$_3$Na, biotin); 2.75 (50/100H+20/100H+5/100H, m, —S—C$\underline{H}_a\underline{H}_b$—CH(OH)—CH$_2$—OH, Sia-H$_{3a}$, biotin); 2.60 (50/100H, dd, 13.5, 7.5 Hz, —S—CH$_a$$\underline{H}_b$—CH(OH)—CH$_2$—OH); 2.55 (2×25/100H, t, 7.0 Hz, —NH—CO—CH$_2$—CH$_2$—C$\underline{H}_2$—S—); 2.30 (2×25/100H, t, 7.0 Hz, —NH—CO—C$\underline{H}_2$—CH$_2$—CH$_2$—S—); 2.21 (2×5/100H, t, 6.5 Hz, biotin); 1.98 (6×20/100H, s, 2×CO—C$\underline{H}_3$); 1.13 (3×20/100H, d, 6.5 Hz, Fuc-H$_6$).

g) Synthesis of Water-soluble Polyaspartamide Derivatives

EXAMPLE C15

Reaction of the Chloroacetic Ester of Poly-(hydroxyethyl)-D/L-Aspartamide B7 With Thioglycerol B7 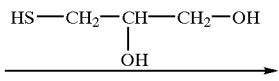

-continued

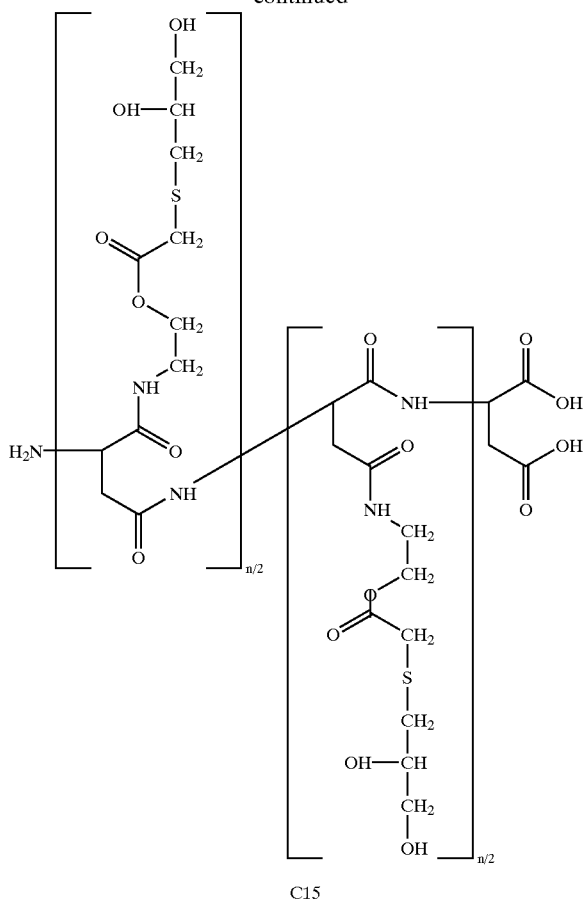

C15

23.5 mg (0.10 mmol) of the chloroacetic ester of poly-(hydroxyethyl)-D/L-aspartamide are dissolved in 1 ml of oxygen-free dimethylformamide at room temperature and under argon. 0.1 ml of thioglycerol and 0.05 ml of triethylamine are added to the clear, colourless solution. After having been stirred at room temperature for 48 h, the clear, colourless solution is added dropwise to 20 ml of diethyl ether/ethanol (1:1). The precipitate which has formed is filtered off and washed with ethanol. The crude product is dissolved in water and this solution is lyophilized. 27 mg (98%) of the polyol C15 are obtained as a colourless solid. n is approximately 250.

$^1$H-NMR (D$_2$O, 250 MHz) δ=4.55 (1H, s (br), CH—CH$_2$); 4.15 (2H, s (br), —NH—CH$_2$—CH$_2$—O—CO—CH$_2$—S—); 3.73 (1H, m, —S—CH$_2$—CH(OH)—CH2OH); 3.50 (2H, m, —S—CH$_2$—CH(OH)—CH$_2$OH); 3.38 (2H, s (br), —NH—CH$_2$—CH$_2$—O—CO—CH$_2$—S—); 3.32 (2H, s, —NH—CH$_2$—CH$_2$—O—CO—CH$_2$—S—); 2.65 (3H, m, —S—CH$_2$—CH(OH)—CH$_2$OH and —CH—CH$_2$—); 2.78–2.25 (2H, m, —CH—CH$_2$—).

D: USES OF POLYMERS

EXAMPLE D1

Ligand Binding Assay For the Determination of IC$_{50}$ Values of Inhibitors of E-selectin E-selectin/human IgG chimera (Ciba-Geigy AG, Basel, SW) is incubated in a Falcon probind™ microtiter plate (Plate 1) at a concentration of 200 ng/well in 0.01M Tris, 0.15 m NaCl, 1 mM CaCl2, pH 7.4 (Tris-Ca$^{++}$ buffer). Thus the plating solution is dispensed as 100 μl/well of 2 μg/ml E-chimera. Row 12 is left blank with only buffer. Plate 1 is incubated covered at 37° C. for 2 hours. After incubation 100 ml/well of 2% BSA in Tris-Ca$^{++}$ buffer is added and incubated at room temperature for 1 hour. During incubation the compounds (2×serial dilution) are titrated in 1% BSA in Tris-Ca$^{++}$ using U-shaped low bind microtiter plates (Plate 2). The rows are serially diluted up to row 9. Rows 10, 11, and 12 contain just buffer. Final volume is 60 ml/well and the first well contains 10 mM of compound with the exception of the positive controls. A (SLex-Lemieux) and B are used as positive controls for each plate and the first well contains 5 mM of these compounds. A polypeptide polymer containing biotin and SLea is conjugated with streptavidin-HRP (KPL, Gaithersburg, Md.) in a molar ratio of 1:2. 60 μl/well of 1 ng/ml of polySLeaSA-HRP (Example C8c) conjugate in 1% BSA in Tris-Ca$^{++}$ are added to all wells except row 11 in Plate 2. Plate 1 is washed four times with Tris-Ca$^{++}$ in the automatic plate washer. 100 μl/well are transferred from Plate 2 to Plate 1 starting from the lowest concentration of compound. Plate 2 is discarded. The plate is incubated while rocking at room temperature for 2 hours. The plate is washed 4 times with Tris-Ca$^{++}$ using an automatic plate washer. 100 ml/well of substrate [mix 3,3',5,5'-tetramethylbenzidine reagent and H$_2$O$_2$ reagent (KPL, Gaithersburg, Md.)] at a 1:1 ratio. The plate is incubated at room temperature for 2 minutes. The reaction is stopped by adding 100 μl/well of 1 M H$_3$PO$_4$ using the 8 channel pipettor from right to left. Absorbance of light at 450 nm is measured in a microtiter plate reader.

The IC$_{50}$ is calculated by determining the concentration of compound required to inhibit maximal binding of the polyS-LeaHRP (Example C8c) conjugate to immobilized E-selectin/human IgG chimera by 50%. The relative IC$_{50}$ is calculated by determining the ratio of the IC$_{50}$ of an internal control compound to the IC$_{50}$ of the test compound.

EXAMPLE D2

Ligand Binding Assay for the Determination of IC$_{50}$ Values of Inhibitors of P-selectin Wells in a microtiter plate (plate1, Falcon probind™) are coated with P-selectin/human IgG chimera (Ciba-Geigy AG, Basel SW) by pre-incubation of wells with 100 μl of 5 mg/ml of goat anti-human Fc antibodies (KPL, Gaithersburg, Md.) in 50 mM Tris, 0.15M NaCl, 2 mM CaCl2, pH 7.4 (Tris-Ca$^{++}$) for 2 hrs at 37° C. followed by washing with Tris-Ca$^{++}$and subsequent incubation with 100 μl of the purified P-selectin chimera at a at a concentration of 200 ng/well. After 2 hours, 100 μl of 2% BSA in Tris-Ca$^{++}$ are added to each well and incubated at 22° C. to block nonspecific binding. During this incubation, inhibitory test compounds (e.g. sLex Lemieux, 5 mM starting concentration), diluted in Tris-Ca$^{++}$, 1% BSA are titrated by a twofold serial dilution in a second U-shaped bottom low-bind microtiter plate (plate 2, Costar Inc.). An equal volume of a preformed complex of biotinylated SLea polypeptide polymer (Example C8c) and horseradish peroxidase-labeled streptavidin (KPL, Gaithersburg, Md.) at 1 μg/ml in Tris-Ca$^{++}$, 1% BSA is added to each well. After 2 hours at 22° C., plate 1 is washed with Tris-Ca$^{++}$ and 100μl/well are transferred from plate 2 to plate 1. The binding reaction is allowed to proceed for 2 hours at 22° C. while gently rocking. Plate 1 is then washed with Tris-Ca$^{++}$ and 100μl of TMB substrate reagent (KPL, Gaithersburg) is added to each well. After three minutes the colorimetrivc reaction is stopped by adding 100 μl/well of H$_3$PO$_4$ and the optical density at 450 nm is determined.

EXAMPLE D3

Assay to Measure Cell Adhesion Under Flow Conditions

Human umbilical vein endothelial cells (huvecs) were isolated from umbilical cords within 12 hours of birth. The umbilical vein was flushed with PBS to remove all blood. The vein was filled with 50 ml of 0.03% collagenase type I (Worthington Biochemicals, LS004196) in RPMI media (Biofluids, MD #313) and incubated for 30 minutes. The collagenase solution was collected from the vein and was washed with an additional 50 ml of PBS which was also collected and added to the collagenase solution. The 100 ml solution was spun at 2000 rpm for 15 min. The supernant was discarded and the cells washed one time with PBS. The cells were suspended in EGM (Clonetics, CA CC3124) and seeded into T-175 flasks (Falcon T-175 flask from Becton-Dickinson) After 24 hours the cells were washed twice in the T-175 flasks with PBS to remove all red blood cells (RBC). Following the washing the cells were cultured in EGM up to 10 days.

When the huvecs reached confluence in the T-175 flasks, they were passaged to 35 mm tissue culture dishes coated with fibronectin (FN) (Gibco 33016-023). The dishes were coated with FN by adding 1 ml of 5.5 $\mu$g/ml FN in PBS to each dish for 30 minutes. The solution was removed prior to seeding the endothelial cells. The huvecs were seeded using a density of $2.2 \times 10^5$ cells / ml and 2–2.5 ml per dish. The dishes were used in 3–5 days once a confluent monolayer was obtained.

Neutrophils were isolated from fresh blood the day of each experiment and used within five hours of the isolation. Normally, 45 mls of blood was collected from healthy adults into 5 mls of sterile sodium citrate (Sigma S-5770). The PMNs were isolated in a single step using the PMN isolation media from Robbins Scientific (1068-00-0). The cells were washed once in 50/50 mixture of Hank's Balanced Salt Solution (HBSS) without Ca and Mg (Sigma H9394) and PBS. The PMNs were suspended in HBSS with Ca and Mg (Sigma H9269) and 12 mM Hepes (Biofluids, MD #305) at $10^7$ cells/ml for use in the flow assay.

Cell Adhesion Flow Assay

A parallel plate flow chamber was used to study the rolling behavior which is characteristic of cells in contact with selectins in the presence of hydrodynamic flow. The parallel plate flow chamber (GlycoTech, Rockville, Md.) with a silicon rubber gasket was of a circular design to accommodate 35 mm tissue culture dishes (Corning) held in place by vacuum. The dimensions of the gasket used in the flow chamber and the volumetric flow rate through the chamber define the wall shear stress for the cells rolling on the huvecs by the following relationship. The wall shear stress ($t_w$, dynes/cm$^2$) is given by $t_w = 6 \mu Q/a^2 b$, where $\mu$ is the apparent viscosity of the media (for H$_2$O @ 37° C.=0.0076P), a is the channel height (i.e. gasket thickness of 254 $\mu$m), b is the channel width (i.e. gasket width of 0.25 cm), and Q is the volumetric flow rate (ml/min).

Prior to the flow assay, the confluent huvec monolayers were stimulated with TNF-a (30 U/ml, Genzyme) for three hours to induce the expression of E-selectin on the cell surface. Multivalent polymers (Example C6a–C6e) were incubated with huvecs and PMNs for 20 minutes prior to flow in the presence of human serum albumin (HSA 3 mg/ml Sigma, A-6784). The cell suspension of PMNs ($10^6$ cells/ml) containing the multivalent polymer was perfused through the chamber at a shear rate corresponding to a wall shear stress of 0.9 dynes/cm$^2$. The cell suspension was allowed to flow through the chamber for three minutes before digital images were collected to quantify each experiment.

Digital Image Acquisition and Analysis

The digital image system consisted of a Silicon Graphics Indigo2 workstation interfacing to Inovision's IC300 digital image system. The cells interacting with the chimera's were visualized using a Zeiss inverted stage microscope (ICM 405) operated in the phase contrast mode using a 10x objective. A CCD camera (Dage-MTI CCD72) was mounted on the microscope to provide the signal to the digital image system. The experiments were recorded on a video recorder (Sony model SVO-1610).

After three minutes of perfusing cells through the flow chamber, digital images were acquired at 7–10 different locations on each of three dishes for every experimental condition. The image acquisition program collected ten images at each location to provide sufficient image data for subsequent image processing. Each of the ten images was a result of a real time minimization function of three frames to remove all moving cells in the bulk flow which are not in contact with huvec monolayer in the flow chamber. Once the ten images were collected, image analysis was performed to generate composite images containing only rolling cells, only arrested cells, or images with the total number of interacting cells (i.e. both the rolling and arrested cells). The images with the rolling cells are created to show the rolling cells as vertical streaks corresponding to the distance traveled by the cells during image acquisition.

The number of interacting cells was determined by a segmentation program based on pixel intensity and size. The digital image analysis system is able to count the number of objects that meet the pixel intensity and size criteria and report the number of interacting cells for each image. The number of arrested cells is usually minimal so they were counted visually. Quantification of the rolling behavior was performed by analysis of images containing the rolling cells as vertical streaks. The measure of rolling was the rolling index defined as the total area (i.e. total pixel count) of all the vertical streaks in each image.

Representative Results

Multivalent polymer (Example C6a) containing 20 mol % sLex (0.1mM per sLex in PMN suspension) was evaluated in above described flow assay. The inhibition of interacting cells was found to be 37% and the inhibition of rolling index was 34%. No effect on arrested cells was observed.

EXAMPLE D4

Use of Polymer to Target Cells Expressing Receptors

Preparation of Cells

Human umbilical vein endothelial cells (huvecs) are isolated and grown in monolayers as described in Example D3. Prior to targeting, the confluent huvec monolayers are stimulated with TNF$\alpha$ (30 U/ml Genzyme) for three hours to induce the expression of E-selectin on the cell surface. Control cultures are not stimulated with TNF$\alpha$.

Preparation of Polymer-bead Complex

Polymer containing biotin and SLea groups (Example C8c) (0.5 ml at 0.5 mg/ml in Tris-Ca$^{++}$) is added to 25 $\mu$l of a suspension (1% solids) of fluorescent latex microspheres labeled with avidin (FluoSpheres$^R$, avidin labeled, 0.03 $\mu$m, Molecular Probes, Eugene, Oreg.). After 30 minutes of incubation at 4° C., beads are separated from excess polymer by centrifugation and washed with Tris-Ca$^{++}$ buffer by repeated centrifugation (3X).

Targeting of Huvecs Expressing Cell Surface E-selectin

Polymer-coated fluorescent beads are added to a monolayer of huvecs to a final dilution of 0.001% solids. The cells are incubated with the beads on ice for I hour. Control conditions include cells not stimulated to express E-selectin and polymer coated beads containing glucose rather than SLea. After incubation the cells are washed with cold Tris-Ca$^{++}$ by gentle aspiration three times and fixed with paraformaldehyde. Fluorescence microscopy revealed specific targeting only of the SLea-containing beads to endothelial cells expressing.

What is claimed is:

1. A linear polypeptide comprising at least two structural elements of the formula

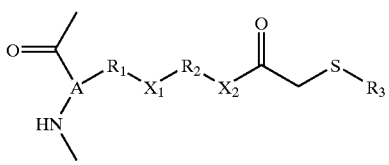 (V)

wherein each A is independently a trivalent, aliphatic hydrocarbon radical having from 1 to 12 carbon atoms which is unsubstituted or substituted by one or more substituents selected from the group consisting of $C_1$–$C_4$-alkyl, $C_1$–$C_4$alkoxy, $C_1$–$C_4$alkylthio, benzyl and benzyloxy;

each $R_1$ is independently a direct bond or $C_1$–$C_6$alkylene;

each $X_1$ is independently —C(O)O—, —C(O)NR—, —NR—, —S— or —O—;

each $R_2$ is independently a bivalent bridging group;

each $X_2$ is independently O or NR; or independently, each $R_2$ and $X_2$ are together a direct bond; and each R is independently H or $C_1$–$C_6$alkyl;

with the proviso that $X_1$ is not —NR—, —S— or —O— when $R_1$ is a direct bond; and each $R_3$ is independently a biological active group which is covalently bound to the S atom either directly or by way of a bridging group Y, wherein at least one $R_3$ is different from another $R_3$.

2. The polypeptide according to claim 1, wherein $R_3$ is selected from the group of radicals derived from alkaloids, carbohydrates, vitamins, peptides, proteins, conjugated proteins, lipids, terpenes, oligonucleotides, antigens, antibodies, a polyhydroxyalkyl or cycloalkyl radical having from 2 to 12 hydroxyl groups which is directly bound to the S atom, and a radical of formula IX —$C_1$–$C_{12}$alkylene-($X_6$)—OH (IX)

which is directly bound to the S atom, wherein $X_6$ is CO, P=O, $SO_2$, $NR_{11}SO_2$ or O—P=O, wherein $R_{11}$ is $C_1$–$C_6$alkyl, or salts of said polypeptide.

3. The polypeptide according to claim 2 wherein at least one $R_3$ is a polyhydroxyalkyl radical having from 2 to 12 hydroxyl groups, a cycloalkyl radical having from 2 to 12 hydroxyl groups, or a radical of formula IX.

4. The polypeptide according to claim 1, wherein at least one $R_3$ is a radical derived from a carbohydrate.

5. The polypeptide according to claim 2, wherein at least one $R_3$ is selected from the group consisting of a polyhydroxyalkyl radical, a cycloalkyl radical, and a radical of formula IX, and at least one $R_3$ is a radical derived from a carbohydrate bound to the S atom by way of a bridging group Y.

6. The polypeptide according to claim 1 wherein at least one $R_3$ is biotinyl.

7. A polypeptide according to claim 1 wherein at least one $R_3$ is sialyl-Lewis x or sialyl-Lewis a.

8. A polypeptide according to claim 1 wherein A is

$R_1$ is —($CH_2$)$_4$—, $X_1$ is NH and $R_2$ and $X_2$ are together a direct bond, or A is

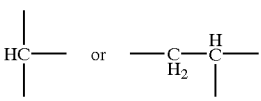

$R_1$ is a direct bond or —$CH_2$—, $X_1$ is —C(O)NH—, $R_2$ is —($CH_2$)$_2$ and $X_2$ is —O—.

9. A method for determining the concentration of a test compound required to inhibit maximal binding of a polypeptide according to claim 1 to an immobilized receptor molecule that binds a polypeptide of claim 1 which comprises:

incubating a polypeptide according to claim 1 in the presence and in the absence of a range of concentrations of test compound with an immobilized receptor molecule that binds a polypeptide of claim 1, determining the degree of binding of the polypeptide of claim 1 in the presence and absence of a range of concentrations of test compound, and determining the concentration of test compound that results in maximal inhibition of binding of the polypeptide to the immobilized receptor molecule.

10. The method according to claim 9, wherein the immobilized receptor molecule is an immobilized E-selectin/human IgG chimera or an immobilized P-selectin/human IgG chimera.

11. A method for targeting a molecule to a cell that expresses a particular receptor which comprises:

preparing a polypeptide according to claim 1, wherein at least one $R_3$ is a ligand which is selectively recognized by a particular receptor and at least one $R_3$ is a molecule to be targeted to a cell that expresses a particular receptor, to provide a modified polypeptide and effecting the binding of the modified polypeptide to the particular receptor on the surface of a cell that expresses the particular receptor.

12. A kit for determining the concentration of a compound that maximally inhibits the binding of a compound of claim 1 to a receptor that binds a compound of claim 1 wherein said kit comprises at least one compound of claim 1, a carrier material, a solid support having affixed thereto a receptor molecule that binds a compound of claim 1, and a detecting system for a complex of a compound of claim 1 with a receptor molecule that binds a compound of claim 1.

13. A method for inhibiting the binding of a first cell to a second cell, wherein said second cell has bound to its surface a receptor, wherein said first cell has bound to its surface a molecule that is bound by said receptor, and wherein a compound of claim 1 also binds to said receptor, comprising contacting said first cell, said second cell, or both said first cell and said second cell concomitantly, with a compound of claim 1, wherein variable $R_3$ is a moiety that inhibits the binding of said molecule to said receptor.

* * * * *